US006936422B2

(12) United States Patent
El Solh et al.

(10) Patent No.: US 6,936,422 B2
(45) Date of Patent: Aug. 30, 2005

(54) POLYNUCLEOTIDES AND THEIR USE FOR DETECTING RESISTANCE TO STREPTOGRAMIN A OR TO STREPTOGRAMIN B AND RELATED COMPOUNDS

(75) Inventors: Nevine El Solh, Vincennes (FR); Jeanine Allignet, Nanterre (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 10/392,970

(22) Filed: Mar. 21, 2003

(65) Prior Publication Data

US 2003/0176679 A1 Sep. 18, 2003

Related U.S. Application Data

(62) Division of application No. 09/099,932, filed on Jun. 19, 1998, now Pat. No. 6,570,001.
(60) Provisional application No. 60/050,380, filed on Jun. 20, 1997.

(51) Int. Cl.[7] .................... C12Q 1/68; C12Q 33/569; G01N 33/53; C12P 19/34; C07H 21/02
(52) U.S. Cl. ..................... 435/6; 435/7.1; 435/91.2; 435/91.1; 435/7.34; 435/975; 536/23.1; 536/24.3; 536/24.32; 536/24.33; 536/23.7
(58) Field of Search ................. 435/6, 7.1, 91.1, 435/91.2, 975; 536/23.1, 24.32, 24.3, 24.33, 23.7

(56) References Cited

U.S. PATENT DOCUMENTS

| | | | |
|---|---|---|---|
| 5,614,395 A | 3/1997 | Ryals et al. | |
| 5,874,224 A | 2/1999 | Bandman et al. | |
| 5,882,888 A | 3/1999 | Jorgensen | |
| 5,994,066 A | 11/1999 | Bergeron et al. | |
| 6,001,564 A | 12/1999 | Bergeron et al. | |
| 6,506,893 B1 | 1/2003 | El Solh et al. | |
| 6,570,001 B1 * | 5/2003 | Solh et al. | 536/23.1 |
| 2002/0102678 A1 * | 8/2002 | Soth et al. | 435/183 |
| 2003/0158135 A1 * | 8/2003 | El Solh et al. | 514/44 |
| 2003/0176679 A1 * | 9/2003 | El Solh et al. | 536/23.1 |

FOREIGN PATENT DOCUMENTS

WO   WO 96/08582   3/1996

OTHER PUBLICATIONS

Jeanine Allignet et al.; "Distribution of Gene Encoding Resistance to Streptogramin A and Related Compounds Among *Staphylococci* Resistant to these Antibiotics," *Antimicrobial Agents and Chemotherapy*, vol. 40(11), pp. 2523–2528; (1996).
Jeanine Allignet et al.; "Sequence of a *Staphylococcal gene, vat*, Encoding an Acetyltransferase Inactivating the A–type Compounds of Virginiamycin–like Antibiotics," *Gene*, vol. 130(1), pp. 91–98; (1993).

Rosanna Rende–Fournier, et al.; "Identification of the *satA* Gene Encoding a Streptogramin A Acetyltransferase in *Enterococcus Faecium* BM4145," *Antimicrobial Agents and Chemotherapy*, vol. 37(10), pp. 2119–2125; (1993).
Jeanine Allignet et al.; "Diversity Among the Gram–Positive Acetyltransferases Inactivating Streptogramin A and Structurally Related Compounds and Characterization of a New Staphylococcal Determinant, vatB," *Antimicrobial Agents and Chemotherapy*, vol. 39(9), pp. 2027–2036; (1995).
Jeanine Allignet et al.; "Distribution of Gene Encoding Resistance to Streptogramin A and Related Compounds Among *Staphylococci* Resistant to these Antibiotics," *Antimicrobial Agents and Chemotherapy*, vol. 40(11), pp. 2523–2528; (1996).
Chang–Kwon Lee et al., "Identification and In Viv Functional Analysis of a Virginiamycin S Resistance Gene (*varS*) from *Streptomyces virginiae*," *J. Bacteriology*, 181/10, pp. 3293–3297; (1999).
Takaaki Hayashi et al., "Characterization of the Human Antizyme Gene," *Gene*, 203, pp. 131–139; (1997).
Sylvie Aubert et al., "Analysis of Two *Staphylococcus epidermidis* Plasmids Coding for Resistance to Streptogramin A," *Plasmid*, 40, pp. 238–242; (1998).
J. I. Ross et al., "Inducible Erythromycin Resistance in *Staphlyococci* is Encoded by a Member of the ATP–Binding Transport Super–Gene Family," *Molecular Microbiology*, 4/7, pp. 1207–1214; (1990).
Joanna Clancy et al., "Molecular Cloning and Functional Analysis of a Novel Macrolide–Resistance Determinant, *mefA*, from *Streptococcus Pyogenes*," *Molecular Microbiology*, 22/5, pp. 867–879; (1996).
David Kovalic et al., "Methylation of Minimalist 23S rRNA Sequences in Vitro by ErmSF (TlrA) N–Methyltransferase," *Biochemistry*, 34, pp. 15838–15844; (1995).
Gerard Lina et al., "Distribution of Genes Encoding Resistance to Macrolides, Lincosamides, and Streptogramins among *Staphylococci*," *Antimicrobial Agents and Chemotherap.*, 43/5, pp. 1062–1066; (1999).

(Continued)

Primary Examiner—N. M. Minnifield
(74) *Attorney, Agent, or Firm*—Finnegan, Henderson, Farabow, Garrett & Dunner, L.L.P.

(57) ABSTRACT

The present invention pertains to polynucleotides derived from *staphylococcal* genes encoding resistance to streptogramin A or to streptogramin B and chemically related compounds. This invention also relates to the use of the polynucleotides as oligonucleotide primers or probes for detecting *Staphylococcal* strains that are resistant to streptogramin A or to streptogramin B and related compounds in a biological sample. In another embodiment, the present invention is directed to the full length coding sequences of the *staphylococcal* genes encoding for resistance to streptogramin A or to streptogramin B from *Staphylococcus* and to the polypeptide expressed by these full length coding sequences. Further, this invention relates to the use of the expressed polypeptides to produce specific monoclonal or polyclonal antibodies that serve as detection means in order to characterize any *staphylococcal* strain carrying genes encoding resistance to streptogramin A or to streptogramin B.

13 Claims, 11 Drawing Sheets

OTHER PUBLICATIONS

Jeanine Allignet and Névine El Solh "Characterization of a New *Staphylococcal* Gene, *vgaB,* Encoding a Putative ABC Transporter Conferring Resistance to *Streptogramin* A and Related Compounds," *Gene*, vol. 202, pp. 133–138; (1997).

Jeanine Allignet, et al. "Nucleotide Sequence of a *Staphylococcal* Plasmid Gene, *vgb*, Encoding a Hydrolase Inactivating the B Components of Virginiamycin–like Antibiotics," *Plasmid*, vol. 20, pp. 271–275; (1988).

Marc Aumercier, et al. "RP 59500: a proposed mechanism for its bactericidal activity," *Journal of Antimicrobial Chemotherapy*, vol. 30, Suppl. A, pp. 9–14; (1992).

N. El Solh, et al. "Epidermiological and Structural Studies of *Staphylococcus aureus* R Plasmids Mediating Resistance to Tobramycin and Streptogramin," *Plasmid*, vol. 4, pp. 117–120; (1980).

Maria Inmaculada Barrasa, et al. "The *ard1* Gene from *Stretomyces capreolus* Encodes a Polypeptide of the ABC–transporters Superfamily which Confers Resistance to the Aminonucleoside Antibiotic A201A," *European Journal of Biochemistry*, vol. 228, pp. 562–569; (1995).

Veronique Blanc, et al. "Molecular Characterization and Transcriptional Analysis of a Multidrug Resistance Gene Cloned from the Pristinamycin–producing Organism, *Streptomyces pristinaespiralis,"* *Molecular Microbiology*, vol. 17, No. 5, pp. 989–999; (1995).

C. Cocito "Antibiotics of the Virginiamycin Family, Inhibitors Which Contain Synergistic Components," *Microbiological Reviews*, vol. 43, No. 2, pp. 145–198; (1979).

M. Di Giambattista, et al. "The Molecular Basis of the Inhibitory Activities of Type A and Type B Synergimycins and Related Antibiotics on Ribosomes," *Journal of Antimicrobial Chemotherapy*, vol. 24, pp. 485–507; (1989).

K.G.H. Dyke and S.P. Curnock, "The Nucleotide Sequence of a Small Cryptic Plasmid Found in *Stapylococcus aureus* and its Relationship to other Plasmids," *FEMS Microbiology Letters*, vol. 58, pp. 209–216; (1989).

J.M. Entenza, et al. "Treatment of Experimental Endocarditis Due to Erythromycin–Suscepitble or –Resistant Methicillin–Resistant *Staphylococcus aureus* with RP 59500," *Antimicrobial Agents and Chemotherapy*, vol. 39, No. 7, p. 1419–1424; (1995).

Bruno Fantin, et al. "Critical Influence of Resistance to Streptogramin B–Type Antibiotics on Activity of RP 59500 (Quinupristin–Dalfopristin) in Experimental Endocarditis Due to *Staphylococcus aureus,"* *Antimicrobial Agents and Chemotherapy*, vol. 39, No. 2, pp. 400–405; (1995).

J. Fernando Fierro, et al. "Streptogramins–inactivating Activity in Three Producer Streptomycetes," *FEMS Microbiology Letters*, vol. 58, pp. 243–246; (1989).

Martin Geistlich, et al. "Characterization of a Novel Regulatory Gene Governing the Expression of a Polyketide Synthase Gene in *Streptomyces ambofaciens,"* *Molecular Microbiology*, vol. 6, No. 14, pp. 2019–2029; (1992).

Maria Griswold, et al. "Quinupristin–dalfopristin (RP 59500): An injectable streptogramin combination," *Am J Health–Syst Pharm*, vol. 53, pp. 2045–2053; (1996).

Stephen Hyde, et al. "Structural Model of ATP–binding Proteins Associated with Cystic Fibrosis, Multidrug Resistance and Bacterial Transport," *Nature*, vol. 346, pp. 362–365; (1990).

Jack Kyte and Russell Doolittle "A Simple Method for Displaying the Hydropathic Character of a Protein," *Journal of Molecular Biology*, vol. 157, pp. 105–132; (1982).

Chang Han Kim, "Studies on Mikamycin B Lactonase: I. Degradation of Mikamycin B by *Streptomyces mitakaensis,"* *The Journal of Antibiotics* vol. XXVII No. 12, pp. 903–908; (1974).

Takeshi Kimura, et al. "Selective Unfolding of Erythroid Chromatin in the Region of the Active β–globin Gene," *Nature*, vol. 306, pp. 709–712; (1983).

Nadia Liassine, Jeanine Allignet, Névine El Solh, et al. "Multiplicity of the Genes and Plasmids Conferring Resistance to Pristina–mycin in *Staphylococci* Selected in an Algerian Hospital," *Zentralblatt für Bakteriologie*, vol. 286, pp. 389–399; (1997).

Jane McLaughlin, et al. "Unique Features in the Ribosome Binding Site Sequence of the Gram–positive *Staphylococcus aureus* β–Lactamase Gene," *The Journal of Biological Chemistry*, vol. 256 No. 21, pp. 11283–11291; (1981).

V. Loncle, et al. "Analysis of Pristinamycin–Resistant *Staphylococcus epidermidis* Isolates Responsible for an Outbreak in a Parisian Hospital," *Antimicrobial Agents and Chemotherapy*, vol. 37, No. 10, pp. 2159–2165; (1993).

Claudia Meyer, et al "Nucleotide Sequence of the Lantibiotic Pep5 Biosynthetic Gene Cluster and Functional Analysis of PepP and PepC—Evidence for a Role of PepC in Thioether Formation," *European Journal of Biochemistry*, vol. 232, pp. 478–489; (1995).

Charles Moran, Jr., et al. "Nucleotide Sequences that Signal the Initiation of Transcription and Translation in *Bacillus subtilis,"* *Mol. Gen. Genet.*, vol. 186, pp. 339–346; (1982).

Carlos Olano, et al. "A Second ABC Transporter is Involved in Oleandomycin Rsistance and its Secretion by *Streptomyces antibioticus,"* *Molecular Microbiology*, vol. 16, No. 2, pp. 333–343; (1995).

Ursula Peschke, et al. "Molecular Characterization of the Lincomycin–production Gene Cluster of *Streptomyces lincolnensis* 78–11," *Molecular Microbiology*, vol. 16, No. 6, pp. 1137–1156; (1995).

Jeremy Ross, et al. "Identification of a Chromosomally Encoded ABC–transport System with which the *Staphylococcal Erythromycin* Exporter MsrA may Interact," *Gene*, vol. 153, pp. 93–98; (1995).

Jeremy Ross, et al., "Minimal Functional System Required for Expression of Erythromycin Resistance by *msrA* in *Staphylococcus aureus* RN4220," *Gene*, vol. 183, pp. 143–148; (1996).

Paul Rosteck, Jr., et al. "Homology between Proteins Controlling *Streptomyces fradiae* Tylosin Resistance and ATP–binding Transport," *Gene*, vol. 102, pp. 27–32; (1991).

Brigitte Schoner, et al. "Sequence Similarity between Macrolide–resistance Determinants and ATP–Binding Transport Proteins," *Gene*, vol. 115, pp. 93–96; (1992).

F. Sanger, et al. "DNA Sequencing with Chain–terminating Inhibitors," *Proc. Natl. Acad. Sci. USA Biochemistry*, vol. 74, No. 12, pp. 5463–5467; (1977).

E.M. Southern "Detection of Specific Sequences Among DNA Fragments Separated by Gel Electrophoresis," *Journal of Molecular Biology*, vol. 98, pp. 503–517; (1975).

Ignacio Tinoco, jun. et al. "Improved Estimation of Secondary Structure in Ribonucleic Acids," *Nature New Biology*, vol. 246, pp. 40–41; (1973).

Margarita Torralba, et al. "Treatment of Methicillin–Resistant *Staphylococcus aureus* Infection with Quinupristin/Dalfopristin," *Clinical Infectious Diseases*, vol. 21, pp. 460–461; (1995).

Gunnar von Heijne "A New Method for Predicting Signal Sequence Cleavage Sites," *Nucleic Acids Research*, vol. 14, No. 11, pp. 4683–4690; (1986).

John Walker, et al. "Distantly Related Sequences in the α– and β–subunits of ATP Synthase, Myosin, kinases and other ATP–requiring Enzymes and a Common Nucleotide Binding Fold," *The EMBO Journal*, vol. 1, No. 8, pp. 945–951; (1982).

Marion E.E. Watson "Compilation of Published Signal Sequences," *Nucleic Acids Research*, vol. 12, No. 13, pp. 5145–5164; (1984).

J. Allignet and N. El Solh "Sequence of a *Staphylococcal* Plasmid Gene *vgaB*, Encoding a Putative ATP–binding Protein Related to VGA Involved in Resistance to Streptogramin A," *National Reference Center For Staphylococci, Institut Pasteur* (P202), p. 239.

Wesley Kloos and Karl Heinz Schleifer "Genus IV. *Staphylococcus* Rosenbach 1884, $18^{AL}$," *Family I. Micrococcaceae*, Section 12. Gram–Positive Cocci, Nom. Cons. Opin. 17 Jud. Comm., 153, pp. 1013–1035; (1958).

* cited by examiner

```
                                    WA
VgaB    -MLKIDMKNVKKYYADKLILNIKELKIYSGDKIGIVGKNGVGKTTLLKIIKGLIEIDEGN     59
Vga     MKIMLEGLNIKHYVQDRLLLNINRLKIYQNDRIGLIGKNGSGKTTLLHILYYKIVPEEG-     59
         . ..  *.*.*  *.*.***  ****  .*.**..****  ******.*.   *  .**

loop 3
VgaB    IIISEKTTIKYISQLEEPHSKIIDGKYASIFQVENKWNDNMSGGEKTRFKLAEGFQDQCS     119
Vga     -IVKQFSHCELIPQLKLIES-----------------TKSGGEVTRNYIRQALDKNPE      99
         *. . .   * **    *                  . ****  **  . .      .

WB
VgaB    LMLVDEPTSNLDIEGIELITNTFKEYRDTFLVVSHDRIFLDQVCTKIFEIENGYIREFIG     179
Vga     LLLADEPTTNLDNNYIEKLEQDLKNWHGAFIIVSHDRAFLDNLCTTIWEIDEGRITEYKG     159
        *.*  ****.***   **  . ..   . .*..*****  ***..**  * **. * *  *.  *

VgaB    NYTNYIEQKEMLLRKQQEEYEKYNSKRKQLEQAIKLKENKAQGMIKPPSKTMGTSES--R     237
Vga     NYSNYVEQKELERHREELEYEKYEKEKKRLEKAINIKEQKAQRATKKP-KNLSLSEGKIK     218
        **.**.****.    ....  *****   .*.**.**  .**.***     * * *.. **   .

VgaB    IWKMQHATKQKKMHRNTKSLETRIDKLNHVEKIKELPSIKMDLPNREQFHGRNVISLKNL     297
Vga     GAKPYFAGKQKKLRKTVKSLETRLEKLESVEKRNELPPLKMDLVNLESVKNRTIIRGEDV     278
         *   *  ****  ...   ****** .** **. ***   **** *  *  ..*...*   .

WA
VgaB    SIKFNNQFLWRDASFVIKGGEKVAIIGNNGVGKTTLLKLILEKVESVIISPSVKIGYVSQ     357
Vga     SGTIEGRVLWKAKSFSIRGGDKMAIIGSNGTGKTTFIKKIVHGNPGISLSPSVKIGYFSQ     338
        *    ..  **   **.*.**.*.****  **  ****   .* *.       .******** **
                                                         loop 3
VgaB    NLDVLQSHKSILENVMSTSIQDETIARIVLARLHFYRNDVHKEINVLSGGEQIKVAFAKL     417
Vga     KIDTLELDKSILENVQSSSQQNETLIRTILARMHFFRDDVYKPISVLSGGERVKVALTKV     398
         .*  *.  ******* *.*  *.   * **.* ..*** **. *  .***.** ***

WB
VgaB    FVSDCNTLILDEPTNYLDIDAVEALEELLITYEGVVLFASHDKKFIQNLAEQLLIIENNK     477
Vga     FLSEVNTLVLDEPTNFLDMEAIEAFESLLKEYNGSIIFVSHDRKFIEKVATRIMTIDNKE     458
        *.*. ***.***** **  *  **.** ** * **   * ..* ***.***.  .*  ... *.*

VgaB    VKKFEGTYIEYLKIKDKPKLNTNEKELKEKKMILEMQISSLLSKISMEENEEKNKELDEK     537
Vga     IKIFDGTY-EQFKQAEKPTRNIKE----DKKLLLETKITEVLSRLSIEPSEE----LEQE     509
         * *.***  *  *   **   *  *     *.**..**  .*.**..*.*  **    *..

VgaB    YKLKLKELKSLNKNI                                              552
Vga     FQNLINEKRNLDK--                                              522
         ..  . * . . *
```

FIG. 3

```
                    Start VgbB
RBS              M N F Y L B R F N L S I P D S G P Y G I T S G E D G K
aggagtttttgcggtcaaatatt gggagatgaatgtaaatgaattttcattagaggggttaactgcctatcccgattcaggtccatcacgtataacctcatcagaagacggaaagg V W F T Q H K A N K I S S L D Q S G R I K B F B V P T P D A K V M C L I V S S L
tatggttcaccaactaggcaaacaaatcagcagtctagatcagagtggtcaggataggataggatcagatcgaaggtaggatcaaagtgatgtgttaattgtatcctccttg
                    XbaI G D I W F T B N G A N K I G K L S K K G G P T B Y P L P Q P D S G P Y G I T B G
gagcatatggtttacagagaatggtgtcaaataaaaagtgcctccaaaagtggctggcttacgaatatccatgtccacagccggattctggtcctacggaataacggaagtc L N G D I M F T Q L N G D R I G K L T A D G T I I Y B Y D L P N K G S Y P A F I T
taaatggcgatatatggtttacccaatgaatggcgatcgtatagaaagttgacagctgacgctgatggactcattatgaatatgattgccaaataaggatcctatcctgtcttattactt L G S D N A L W F T B N Q N N S I G R I T N T G K L B B Y P L P T N A A A P V G
taggtcggataaacgcacttggttcacggagaaccaaaataattcattggaaggattacaaatacgggaatttagaagaatatccctaccaacaaatgcagcggtccgtgggta I T S G N D G A L W F V B I N G N K I G R I T T T G B I S B Y D I P T P N A R P
tcactagtggtaacgatggtgcacctgtggttttgtcgaactctatagtgggcaacaaaatatggtcgatcactacaactggtgagatatgtgcgatatgattccaactcaaacgacgtccac H A I T A G K N S B I W F T B N G A N Q I G R I T N D K T I Q B Y Q L Q T B N A
agctataaccgcggggaaaaatagcgaaatatggttactgaatgggggcaaatcaaatcgcagaatcaaacgacaaacaattcaagatatcaacttcaaacagaaaatgcgg Start vgtC
R P H G I T F G K D G S V W F A L K C K I G K L N L N B .  M K W Q N
aacctcatggtattacccttggaaagatcgatccgtatgcttgcatcaaaatgtcaaattggaagctgaatgatggaggagcaatatttatgaatggagcaaaa
              BamHI                                  END VgbB     RBS +

Q Q G P N B B I Y P I B G N K H V Q P I T K P N I L V G B Y S Y Y D S
tcagcaaggccccaatccaggagaaatatacccctattaacatgttcattcattaaaccatctataaccaaagccaatatttcagttggggaatattcatattacgatag K D G B S P B S Q V L Y H Y B L I G D K L I L G K F C S I G P T T P I H N G A
taaagatggtgaatccttttcgaagccaagtcttaatcaccatgaatctgatggggtaaactactaattagggaagtttgtctattggaccggaacgacattataatgaatgggc N H R M D G S T P P H L F G N G W B K H T P T L B D L P Y K G N T B I G N D V
taatcatcgtatgtgatggtgttcaatcattccattcaatctttttcggagaatggtgggagaagcatcaccctataccattggaagaccttcattggaagtaacacggaaattgggaacgatgt W I G R D V T I M P G V K I G N G A I I A A K S V V T K N V D P Y S V V G G N P
tgggattggacgagatgtgacaattatgccggtgtcaaaaatagggaacgggcctattattgcagcaaaatcggttgcaagaacgttgatcctattcagtgtggcggtaatcc G R L I K I R P S K B K I A A L L K V R N W D L B I B T I N B W I D C I L N G D
tccacgattaattaagatcgtttcccaaggaaaaatcgcagcactactaaaagtaaggtgtgggacctagatagagacagagacgataatgaaatattgatgattgcatccgtgaatggtga I K K V K R S .
tataaaaaaagcgttaaaacttgaaaacgaaattgttaggtta
End vgtC
```

FIG. 5

PCR PRIMERS vatC

Oligo III        5'-at<u>gaattc</u>gcaaatcagcaagg-3'
                      EcoRI Oligo IV         5'-tcgtctc<u>gagctc</u>taggtcc-3'
                            SacI

FIG. 6A vgbB

Oligo V          5'-cagcag<u>tctaga</u>tcagagtgg-3'
                          XbaI Oligo VI         5'-catac<u>ggatcc</u>acctttcc-3'
                         BamHI

FIG. 6B vgaB

Oligo I          5'-AAGTCGACTGACAATATGAGTGGTGG-3'

Oligo II         5'-CTGCAGATGCCTCAACAGCATCGATATCC-3'

FIG. 6C

SEQ ID NO: 1

*Seq vgaB*
ATGCTTAAAATCGACATGAAGAATGTAAAAAAATATTATGCAGATAAATTAATTTTAAATATAAA
AAAGATTTATAGTGGGGATAAAATAGGTATTGTAGGTAAGAATGGAGTTGGCAAAACAACACTTT
TAATAAAAGGACTAATAGAGATTGACGAAGGAAATATAATTATAAGTGAAAAAACAACTATTAAA
TCTCAATTAGAAGAACCACATAGTAAGATAATTGATGGAAAATATGCTTCAATATTTCAAGTTGA
GTGGAATGACAATATGAGTGGTGGTGAAAAAACTAGATTTAAACTAGCAGAGGGATTTCAAGATC
CTTTAATGCTCGTAGATGAACCTACAAGTAATTTAGATATCGAAGGAATAGAGTTGATAACAAAT
AAAGAGTACCGTGATACTTTTTTGGTAGTATCTCATGATAGAATTTTTTTAGATCAAGTTTGTAC
TTTTGAAATTGAAAATGGATATATTAGAGAATTCATCGGTAATTATACAAACTATATAGAGCAAA
TGCTTCTACGAAAGCAACAAGAAGAATACGAAAGTATAATTCTAAAAGAAAGCAATTGGAGCAA
AAGCTAAAAGAGAATAAGGCGCAAGGAATGATTAAGCCCCCTTCAAAAACAATGGGAACATCTGA
AATATGGAAAATGCAACATGCTACTAAACAAAAAAAGATGCATAGAAATACGAAATCGTTGGAAA
TAGATAAATTAAATCATGTAGAAAAAATAAAAGAGCTTCCTTCTATTAAAATGGATTTACCTAAT
CAATTTCATGGTCGCAATGTAATTAGTTTAAAAAACTTATCTATAAAATTTAATAATCAATTTCT
AGATGCTTCATTTGTCATTAAAGGTGGAGAAAAGGTTGCTATAATTGGTAACAATGGTGTAGGAA
CATTGTTGAAGCTGATTCTAGAAAAAGTAGAATCAGTAATAATATCACCATCAGTTAAAATTGGA
AGTCAAAACTTAGATGTTCTACAATCTCATAAATCTATCTTAGAAAATGTTATGTCTACCTCCAT
TGAAACAATAGCAAGAATTGTTCTAGCAAGATTACATTTTTATCGCAATGATGTTCATAAAGAAA
TTTTGAGTGGTGGAGAACAAATAAAGGTTGCTTTTGCCAAGCTATTTGTTAGCGATTGTAATACA
CTTGATGAACCAACAAACTATTTGGATATCGATGCTGTTGAGGCATTAGAAGAATTGTTAATTAC
AGGTGTTGTGTTATTTGCTTCCCATGATAAAAAATTTATACAAAACCTAGCTGAACAATTGTTAA
AAAATAATAAAGTGAAAAAATTCGAAGGAACATATATAGAATATTTAAAAAATTAAAGATAAACCA
AATACAAATGAAAAAGAACTCAAAGAAAAAAAGATGATACTAGAAATGCAAATTTCATCATTATT
AATCTCAATGGAAGAAAATGAAGAAAAAAACAAAGAATTAGATGAAAAGTACAAATTGAAATTAA
TGAAAAGCCTAAATAAAAATATT

SEQ ID NO: 3

*Seq vgbB*
ATGAATTTTTATTTAGAGGAGTTTAACTTGTCTATTCCCGATTCAGGTCCATACGGTATAACTTC
AGACGGAAAGGTATGGTTCACACAACATAAGGCAAACAAAATCAGCAGTCTAGATCAGAGTGGTA
AAGAATTCGAAGTTCCTACCCCTGATGCTAAAGTGATGTGTTTAATTGTATCTTCACTTGGAGAC
TTTACAGAGAATGGTGCAAATAAAATCGGAAAGCTCTCAAAAAAAGGTGGCTTTACAGAATATCC
ACAGCCGGATTCTGGTCCTTACGGAATAACGGAAGGTCTAAATGGCGATATATGGTTTACCCAAT
GAGATCGTATAGGAAAGTTGACAGCTGATGGGACTATTTATGAATATGATTTGCCAAATAAGGGA
CCTGCTTTTATTACTTTAGGTTCGGATAACGCACTTTGGTTCACGGAGAACCAAAATAATTCTAT
GATTACAAATACAGGGAAATTAGAAGAATATCCTCTACCAACAAATGCAGCGGCTCCAGTGGGTA
GTGGTAACGATGGTGCACTCTGGTTTGTCGAAATTATGGGCAACAAAATAGGTCGAATCACTACA
GAGATTAGCGAATATGATATTCCAACTCCAAACGCACGTCCACACGCTATAACCGCGGGGAAAAA
AATATGGTTTACTGAATGGGGGGCAAATCAAATCGGCAGAATTACAAACGACAAAACAATTCAAG
AACTTCAAACAGAAAATGCGGAACCTCATGGTATTACCTTTGGAAAAGATGGATCCGTATGGTTT
AAATGTAAAATTGGGAAGCTGAATTTGAACGAA

FIG. 7A

SEQ ID NO: 2

SEQ vatC
ATGAAATGGCAAAATCAGCAAGGCCCCAATCCAGAAGAAATATACCCTATAGAAGGTAATAAAC
AATTTATTAAACCATCTATAACAAAGCCCAATATTTTAGTTGGGGAATATTCATATTACGATAG
TGGTGAATCTTTTGAAAGCCAAGTTCTTTATCACTATGAATTGATTGGGGATAAACTAATATTA
TTTTGTTCTATTGGACCCGGAACGACATTTATAATGAATGGGGCTAATCATCGTATGGATGGTT
TTCCATTCAATCTTTTCGGAAATGGTTGGGAGAAGCATACCCCTACATTGGAAGACCTTCCTTA
TAACACGGAAATTGGGAACGATGTTTGGATTGGACGAGATGTGACAATTATGCCCGGTGTAAAA
AACGGGGCTATTATTGCAGCAAAATCGGTTGTGACAAAGAACGTTGATCCTTATTCAGTTGTTG
ATCCTTCACGATTAATTAAGATAAGGTTTTCCAAGGAAAAAATCGCAGCATTACTAAAAGTAAG
GGACCTAGAGATAGAGACGATAAATGAAAATATTGATTGCATCCTGAATGGTGATATAAAAAAG
AGAAGT

FIG. 7B

SEQ ID NO: 4

VgaB
MLKIDMKNVKKYYADKLILNIKELKIYSGDKIGIVGKNGVGKTTLLKIIK
GLIEIDEGNIIISHKTTIKYISQLEEPHSKIIDGKYASIFQVENKWNDNM
SGGEKTRFKLAEGFQDQCSLMLVDEPTSNLDIEGIELITNTFKEYRDTFL
VVSHDRIFLDQVCTKIFEIENGYIREFIGNYTNYIEQKEMLLRKQQEEYE
KYNSKRKQLEQAIKLKENKAQGMIKPPSKTMGTSESRIWKMQHATKQKKM
HRNTKSLETRIDKLNHVEKIKELPSIKMDLPNREQFHGRNVISLKNLSIK
FNNQFLWRDASFVIKGGEKVAIIGNNGVGKTTLLKLILEKVESVIISPSV
KIGYVSQNLDVLQSHKSILENVMSTSIQDETIARIVLARLHFYRNDVHKE
INVLSGGEQIKVAPAKLPVSDCNTLILDEPTNYLDIDAVEALEELLITYE
GVVLFASHDKKPIQNLAEQLLIIENNKVKKFEGTYIEYLKIKDKPKLNTN
EKELKEKKMILEMQISSLLSKISMEENEEKNKGLDEKYKLKLKELKSLNK
NI

SEQ ID NO: 6

VgbB
MNFYLEEFNLSIPDSGPYGITSSEDGKVWFTQHKANKISSLDQSGRIKEF
EVPTPDAKVMCLIVSSLGDIWFTENGANKIGKLSKKGGFTEYPLPQPDSG
PGITEGLNGDIWFTQLNGDRIGKLTADGTIYEYDLPNKGSYPAFITLGSD
NALWFTENQNNSIGRITNTGKLEEYPLPTNAAAPVGITSGNDGALWFVEI
MGNKIGRITTTGEISEYDIPTPNARPHAITAGKNSEIWFTEWGANQIGRI
TNDKTIQEYQLQTENAEPHGITFGKDGSVWFALKCKIGKLNLNE

SEQ ID NO: 5

VatC
MKWQNQQGPNPEEIYPIEGNKHVQFIKPSITKPNILVGEYSYYDSKDGES
FESQVLYHYELIGDKLILGKFCSIGPGTTFIMNGANHRMDGSTFPFNLFG
NGWEKHTPTLEDLPYKGNTEIGNDVWIGRDVTIMPGVKIGNGAIIAAKSV
VTKNVDPYSVVGGNPSRLIKIRFSKEKIAALLKVRWWDLEIETINENIDC
ILNGDIKKVKRS

FIG. 7C

```
SEQ ID NO: 7            K   S   I   L   E   N   V                    VgaB
                     1795                    1815
SEQ ID NO: 11     5' - aaa tct atc tta gaa aat gtt -3'                vgaB
                         g   agc  t SEQ ID NO: 8            N   Y   T   N   Y   I   E   Q   K   E        VgaB
                                S           V
                     1237                                    1266
SEQ ID NO: 12     5' - aat tat aca aac tat ata gag caa aaa gaa -3'    vgaB
                               gt          gtt  a SEQ ID NO: 9            I   M   N   G   A   N   H   R   M            VatC
                                        a   c   a   a
                     1187                                1213
SEQ ID NO: 13     5' - ata atg aat ggg gct aat cat cgt atg -3'        vatC
                       t           t   a   c       g SEQ ID NO: 10           G   N   D   V   W   I   G                    VatC
                     1310 a   t   g           t 1330
SEQ ID NO: 14     5' - ggg aac gat gtt tgg att gga - 3'               vatC
                           a   t   a       a   t
```

FIG. 7D

POLYNUCLEOTIDES AND THEIR USE FOR DETECTING RESISTANCE TO STREPTOGRAMIN A OR TO STREPTOGRAMIN B AND RELATED COMPOUNDS

CROSS-REFERENCE TO RELATED APPLICATIONS

This is a divisional application of application Ser. No. 09/099,932, filed Jun. 19, 1998 now U.S. Pat. No. 6,570,001, which claims the benefit under 35 U.S.C. § 119(e) of U.S. Provisional Application No. 60/050,380, filed Jun. 20, 1997, the disclosures of each of which are incorporated herein by reference.

BACKGROUND OF THE INVENTION

The present invention pertains to polynucleotides derived from *staphylococcal* genes encoding resistance to streptogramin A or to streptogramin B and chemically related compounds. This invention also relates to the use of the polynucleotides as oligonucleotide primers or probes for detecting *Staphylococcal* strains that are resistant to streptogramin A or to streptogramin B and related compounds in a biological sample.

In another embodiment, the present invention is directed to the full length coding sequences of the *staphylococcal* genes encoding for resistance to streptogramin A or to streptogramin B from *Staphylococcus* and to the polypeptides expressed by these full length coding sequences.

Further, this invention relates to the use of the expressed polypeptides to produce specific monoclonal or polyclonal antibodies that serve as detection means in order to characterize any *staphylococcal* strain carrying genes encoding resistance to streptogramin A or to streptogramin B.

The present invention is also directed to diagnostic methods for detecting specific strains of *Staphylococcus* expected to be contained in a biological sample. The diagnostic methods use the oligonucleotide probes and primers as well as the antibodies of the invention.

Streptogramins and related compounds (antibiotics) produced by *streptomycetes* can be classified as A and B compounds according to their basic primary structures (Cocito, 1979). Compounds of the A group, including streptogramin A (SgA), pristinamycin IIA (PIIA), virginiamycin M, mikamycin A, or synergistin A, are polyunsaturated cyclic macrolactones. Compounds of the B group, including streptogramin B (SgB), pristinamycin B (PIB), virginiamycin S, mikamycin B, and synergistin B, are cyclic peptidic macrolactones (Cocito, 1979). Compounds of both groups, A and B, bind different targets in the peptidyltransferase domain of the 50S ribosomal subunit and inhibit protein elongation at different steps (Aumercier et al., 1992; Di Giambattista et al., 1989).

A decrease in the dissociation constant of PIB is observed in the presence of PIIA because this latter antibiotic provokes a conformational modification of the bacterial ribosome at the binding sites of these molecules. Thus, A and B compounds, which are bacteribstatic when used separately, act synergistically when combined and become bactericidal, mainly against Gram-positive bacteria.

Natural mixtures such as pristinamycin (Pt), synergistin, virginiamycin and mikamycin, are used orally and topically. A semi-synthetic injectable streptogramin, RP59500, consisting of a mixture of derivatives of A and B compounds (Dalfopristin and Quinupristin, respectively) is currently undergoing in vivo experimental and clinical trials (J. Antimicrob. Agents Chemother. 30 (Suppl. A), entire volume, 1992; Entenza et al., 1995; Fantin et al., 1995; Griswold et, al., 1996; Torralba et al., 1995). *Staphylococcal* resistance to synergistic mixtures of A and B compounds (Pt MIC$\geq$2 µg/ml) is always associated with resistance to A compounds (PIIA MIC$\geq$8 µg/ml), but not necessarily with resistance to B compounds (Allignet et al., 1996).

To date, four genes encoding resistance to A compounds have been isolated from *staphylococcal* and enterococcal plasmids. The genes vat (Allignet et al., 1993), vatB (Allignet and El Solh, 1995), and satA (Rende-Fournier et al., 1993) encode related acetyltransferases (50.4–58.3% amino acids), which inactivate streptogramin A and similar compounds. The *staphylococcal* gene vga (Allignet et al., 1992) encodes an ATP-binding protein probably involved in the active efflux of A compounds. Nevertheless, there continues to exist a need in the art for polynucleotides specific for *Staphylococcus* resistant to streptogramin A and/or B and related compounds.

SUMMARY OF THE INVENTION

Accordingly, this invention aids in fulfilling this need in the art. In particular, this invention provides a purified peptide comprising an amino acid sequence selected from the group consisting of:
  a) SEQ ID NO: 4 which corresponds to the complete amino acid sequence of Vga B or fragments derived from SEQ ID NO: 4 containing at least 10 amino acids;
  b) SEQ ID NO: 5 which corresponds to the complete amino acid sequence of Vat C or fragments derived from SEQ ID NO: 5 containing at least 10 amino acids;
  c) SEQ ID NO: 6 which corresponds to the complete amino acid sequence of Vgb B or fragments derived from SEQ ID NO: 6 containing at least 10 amino acids;
  d) SEQ ID NO: 7 which corresponds to a fragment of the amino acid sequence of Vgb B;
  e) SEQ ID NO: 8 which corresponds to a fragment of the amino acid sequence of Vga B;
  f) SEQ ID NO: 9 which corresponds to a fragment of the amino acid sequence of Vat C; and
  g) SEQ ID NO: 10 which corresponds to a fragment of the amino acid sequence of Vat C.

This invention additionally provides a purified polynucleotide comprising the nucleotide sequence selected from the group consisting of:
  a) SEQ ID NO: 1 which corresponds to the complete nucleic acid sequence of vga B or fragments derived from SEQ ID NO: 1 containing 15 to 40 nucleotides;
  b) SEQ ID NO: 2 which corresponds to the complete nucleic acid sequence of vat C or fragments derived from SEQ ID NO: 2 containing 15 to 40 nucleotides;
  c) SEQ ID NO: 3 which corresponds to the complete nucleic acid sequence of vgb B or fragments derived from SEQ ID NO: 3 containing 15 to 40 nucleotides;
  d) SEQ ID NO: 11 which corresponds to the nucleic acid sequence encoding the polypeptide of SEQ ID NO: 7;
  e) SEQ ID NO: 12 which corresponds to the nucleic acid sequence encoding the polypeptide of SEQ ID NO: 8;
  f) SEQ ID NO: 13 which corresponds to the nucleic acid sequence encoding the polypeptide of SEQ ID NO: 9; and
  g) SEQ ID NO: 14 which corresponds to the nucleic acid sequence encoding the polypeptide of SEQ ID NO: 10.

Furthermore, this invention includes a purified peptide comprising the amino acid sequence encoded by the nucleotide sequence selected from the group consisting of:

a) SEQ ID NO: 1,
b) SEQ ID NO: 2,
c) SEQ ID NO: 3,
d) SEQ ID NO: 11,
e) SEQ ID NO: 12,
f) SEQ ID NO: 13, and
g) SEQ ID NO: 14.

This invention also provides a composition comprising purified polynucleotide sequences including at least one nucleotide sequence of the genes selected from the group consisting of polypeptides or genes or cDNA of vgaB, vatC, and vgbB, which are useful for the detection of resistance to streptogramin A or to streptogramin B and related compounds.

In another embodiment, this invention provides a composition of polynucleotide sequences encoding resistance to streptogramins and related compounds, or inducing this resistance in Gram-positive bacteria, wherein the composition comprises a combination of at least two of the following nucleotide sequences: a) a nucleotide sequence encoding an acetyltransferase conferring resistance to streptogramin A and related compounds, b) a nucleotide sequence encoding a molecule containing ATP binding motifs conferring resistance to streptogramin A and related compounds; and c) a nucleotide sequence encoding a lactonase conferring resistance to streptogramin B and related compounds.

Furthermore, this invention provides a composition of polynucleotide sequences, wherein the sequence encoding a molecule containing ATP binding motifs confers resistance to *Staphylococci* and particularly to *S. aureus*, and wherein the polynucleotide sequence corresponds to a vgaB nucleotide sequence represented by SEQ ID NO: 1 or a sequence having at least 70% homology with vgaB complete nucleotide sequence, or to a polynucleotide hybridizing with SEQ ID NO: 1 under stringent conditions, or to a fragment containing between 20 and 30 nucleotides of SEQ ID NO: 11 or SEQ ID NO: 12, or wherein the polynucleotide sequence encodes a polypeptide having at least 60% homology with the complete SEQ ID NO: 4 or with SEQ ID NO: 7 or SEQ ID NO: 8.

Furthermore this invention relates to a composition of polynucleotide sequences, wherein the sequence encoding an acetyltransferase confers resistance to streptogramin A and related compounds in *Staphylococci*, and particularly in *S. cohnii*, and wherein the polynucleotide sequence corresponds to a vatC nucleotide sequence represented by SEQ ID NO: 2 or a sequence having at least 70% homology with vatC complete nucleotide sequence, or to a polynucleotide hybridizing with SEQ ID NO: 2 under stringent conditions, or to a fragment containing between 20 and 30 nucleotides of SEQ ID NO: 13 or SEQ ID NO: 14, or wherein the polynucleotide sequence encodes a polypeptide having at least 60% homology with the complete SEQ ID NO: 5 or with SEQ ID NO: 9 or SEQ ID NO: 10.

This invention also provides a composition of polynucleotide sequences, wherein the sequence encoding a lactonase confers resistance to streptogramin B and related compounds in *Staphylococci* and particularly in *S. cohnii*, and wherein the polynucleotide sequence corresponds to a vgbB nucleotide sequence represented in SEQ ID NO: 3 or a sequence having at least 70% homology with vgbB complete nucleotide sequence, or to a polynucleotide hybridizing with SEQ ID NO: 3 under stringent conditions, or to a fragment containing between 20 and 40 nucleotides of SEQ ID NO: 3, or wherein the polynucleotide sequence encodes a polypeptide having at least 60% homology with the complete SEQ ID NO: 6.

The invention also contemplates a composition of polynucleotide sequences, wherein at least a vatB nucleotide sequence encoding an acetyltransferase conferring resistance to streptogramin A and related compounds is included in addition to a vgaB nucleotide sequence encoding a molecule containing ATP binding motifs conferring resistance to streptogramin A.

Additionally, the invention includes a purified polynucleotide that hybridizes specifically under stringent conditions with a polynucleotide sequence selected from the group consisting of SEQ ID NO: 1, SEQ ID NO: 2, SEQ ID NO: 3, SEQ ID NO: 11, SEQ ID NO: 12, SEQ ID NO: 13, and SEQ ID NO: 14.

The invention further includes polynucleotide fragments comprising at least 10 nucleotides capable of hybridization under stringent conditions with any one of the nucleotide sequences enumerated above.

In another embodiment of the invention, a recombinant DNA sequence comprising at least one nucleotide sequence enumerated above and under the control of regulatory elements that regulate the expression of resistance to antibiotics of the streptogramin family in a defined host is provided.

Furthermore, the invention includes a recombinant vector comprising the recombinant DNA sequence noted above, wherein the vector comprises the plasmid pIP1633 or plasmid pIP1714.

The invention also includes a recombinant cell host comprising a polynucleotide sequence enumerated above or the recombinant vector defined above.

In still a further embodiment of the invention, a method of detecting bacterial strains that contain the polynucleotide sequences set forth above is provided.

Additionally, the invention includes kits for the detection of the presence of bacterial strains that contain the polynucleotide sequences set forth above.

The invention also contemplates antibodies recognizing peptide fragments or polypeptides encoded by the polynucleotide sequences enumerated above.

Still further, the invention provides for a screening method for active antibiotics and/or molecules for the treatment of infections due to Gram-positive bacteria, particularly *staphylococci*, based on the detection of activity of these antibiotics and/or molecules on bacteria having the resistance phenotype to streptogramins.

It is to be understood that both the foregoing general description and the following detailed description are exemplary and explanatory only and are not restrictive of the invention, as claimed.

BRIEF DESCRIPTION OF THE DRAWINGS

This invention will be more fully described with reference to the drawings in which:

FIG. 2 is the nucleotide sequence and deduced amino acid sequence of 2411 nucleotides from pIP1633, which contains the gene vgaB of *S. aureus* conferring resistance to streptogramin A and related compounds. The putative ribosome binding site (RBS) is underlined. The amino acids are aligned with the second nucleotide of each codon. Asterisks indicate the in-frame stop codons. The A and B ATP-binding motifs described by Walker et al. (1982) and detected within each of the two ATP-domains are boxed. The conserved motif SGG of the two copies of loop 3 described by Hyde et al. (1990) is underlined. Relevant restriction sites are shown.

FIG. 3 is the amino acid sequence alignment of the predicted 60 and 61 kDa proteins encoded by Vga (Allignet et al., 1992, accession No: m90056) and VgaB (FIG. 2), respectively. Identical residues are indicated by asterisks and conservative changes are shown by single dots. The A and B motifs of Walker et al. (1982) are in bold type (WA, WB). The conserved motif SGG of the two copies of loop 3 described by Hyde et al. (1990) is underlined.

FIG. 5 is the nucleotide sequence and deduced amino acid sequence of 1727 nucleotide from pIP1714, which contains the gene vgbB and vatC of *S. cohnii*. Relevant restriction sites are shown.

FIGS. 6A, 6B, and 6C represent oligonucleotide primers for hybridization under stringent conditions with vatC, vgbB, and vgaB respectively.

FIG. 7 represents SEQ ID NOs: 1–14.

DETAILED DESCRIPTION OF THE INVENTION

Figures 1A, 1B:
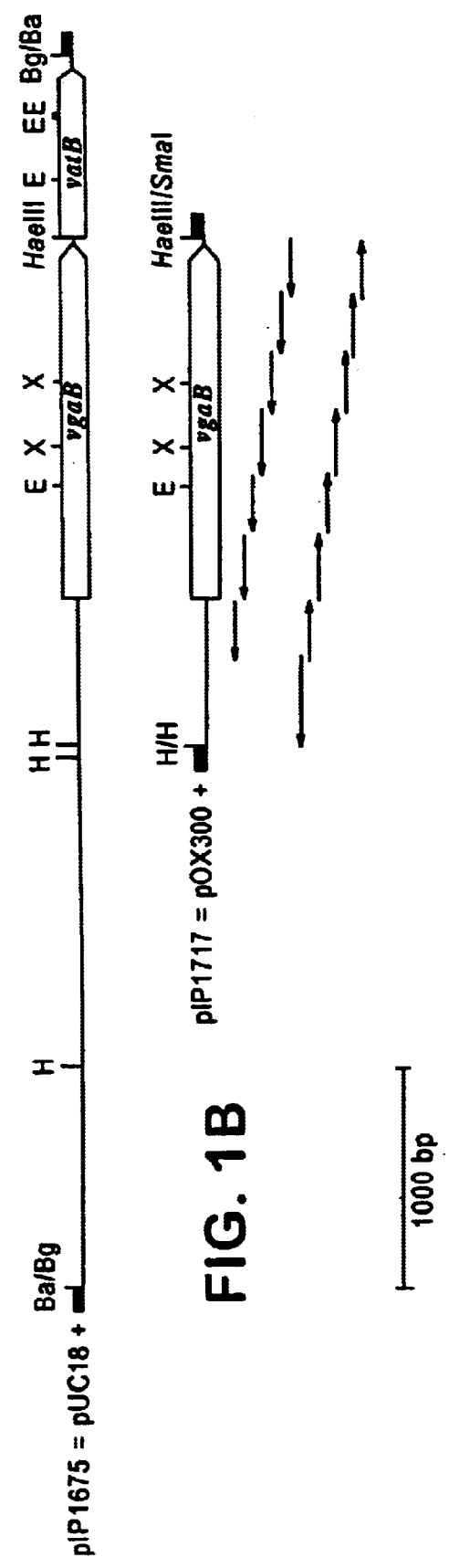
FIGS. 1A and 1B are the restriction maps of the 5.5 kb BglII fragment and of the 2.4 kb HindIII-HaeIII fragment of pIP1633, respectively. Both fragments confer resistance to streptogramin A and related compounds. The strategy for sequencing the 2.4 kb HindIII-HaeIII fragment is given in FIG. 1B. Restriction enzyme abbreviations: Ba, BamHI; Bg, BglII; E, EcoRI; H. HindIII; X, XbaI.

It has now been determined that bacteria from the *Staphylococcus* genus carry a vgaB gene, which encodes a putative ATP-binding protein that confers resistance to streptogramin A and structurally similar compounds. It has also now been determined that bacteria from the *Staphylococcus* genus carry a vgbB gene, which encodes a lactonase that confers resistance to streptogramin B and structurally similar compounds, and a vatC gene, which encodes an acetyltransferase that confers resistance to streptogramin A and structurally similar compounds.

Novel polynucleotides corresponding to the vgaB, vgbB, and vatC genes from various strains of *Staphylococcus* have been isolated and sequenced, and it has been surprisingly demonstrated that these new polynucleotides make it possible to design oligonucleotide probes or primers. These polynucleotides include the following:

a) SEQ ID NO: 1,
b) SEQ ID NO: 2,
c) SEQ ID NO: 3,
d) SEQ ID NO: 11,
e) SEQ ID NO: 12,
f) SEQ ID NO: 13, and
g) SEQ ID NO: 14.

This invention provides specific pairs of oligonucleotide primers or probes that hybridize specifically, under stringent hybridization conditions as defined hereinafter, to the nucleic acid (RNA or DNA) from a particular strain of the *Staphylococcus* genus. These oligonucleotide primers include the following:

a)
Oligo I       5'´AAGTCGACTGACAATATGAGTGGTGG-3'

Oligo II      5'-CTGCAGATGCCTCAACAGCATCGATATCC-3'

-continued b)
Oligo III     5'-ATGAATTCGCAAATCAGCAAGG-3'

Oligo IV      5'-TCGTCTCGAGCTCTAGGTCC-3' c)
Oligo V       5'-CAGCAGTCTAGATCAGAGTGG-3'

Oligo VI      5'-CATACGGATCCACCTTTTCC-3'.

In a specific embodiment of the present invention, the purified polynucleotides useful for detecting *Staphylococcal* strains can be used in combination in order to detect bacteria belonging to *Staphylococci* in a biological sample. Thus, the present invention also provides detection methods and kits comprising combinations of the purified polynucleotides according to the invention. The purified oligonucleotides of the invention are also useful as primers for use in amplification reactions or as nucleic acid probes.

By "polynucleotides" according to the invention is meant the sequences referred to as SEQ ID NOS: 1–14 and the complementary sequences and/or the sequences of polynucleotides which hybridize to the referred sequences under high stringent conditions and which are used for detecting *staphylococcal* strains carrying a gene encoding resistance to streptogramin A or to streptogramin B.

By "active molecule" according to the invention is meant a molecule capable of inhibiting the activity of the purified polypeptide as defined in the present invention or capable of inhibiting the bacterial culture of *staphylococcal* strains.

Thus, the polynucleotides of SEQ ID NOs: 1–3 and 11–14 and their fragments can be used to select nucleotide primers notably for an amplification reaction, such as the amplification reactions further described.

PCR is described in the U.S. Pat. No. 4,683,202 granted to Cetus Corp. The amplified fragments may be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic probes the polynucleotides of SEQ ID NOs: 1–3 and 11–14 and their fragments, oligonucleotides that are complementary to these polynucleotides or fragments thereof, or their amplification products themselves.

Amplified nucleotide fragments are useful as probes in hybridization reactions in order to detect the presence of one polynucleotide according to the present invention or in order to detect the presence of a bacteria of *Staphylococcal* strain carrying genes encoding resistance to streptogramin A or streptogramin B, in a biological sample. This invention also provides the amplified nucleic acid fragments ("amplicons") defined herein above. These probes and amplicons can be radioactively or non-radioactively labeled, using for example enzymes or fluorescent compounds.

Preferred nucleic acid fragments that can serve as primers according to the present invention are the following:

polynucleotides of sequence SEQ ID NOs: 1–3 and 11–14; and polynucleotides having a length from 20 to 30 consecutive nucleotides from a polynucleotide selected from the group consisting of polynucleotides of sequences SEQ ID NO: 11 to SEQ ID NO: 14 or from 20 to 40 consecutive nucleotides from a polynucleotide of SEQ ID NO: 3

The primers can also be used as oligonucleotide probes to specifically detect a polynucleotide according to the invention.

Other techniques related to nucleic acid amplification can also be used and are generally preferred to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme and on the property of this DNA polymerase to displace the previously synthesized strand being localized downstream.

The SDA amplification technique is more easily performed than PCR (a single thermostated water bath device is necessary), and is faster than the other amplification methods. Thus, the present invention also comprises using the nucleic acid fragments according to the invention (primers) in a method of DNA or RNA amplification according to the SDA technique. The polynucleotides of SEQ ID NOs: 1–3 and 11–14 and their fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990;

NASBA (Nucleic acid Sequence Based Amplification), described by Kievitis et al. in 1991; and TMA (Transcription Mediated Amplification).

The polynucleotides of SEQ ID NOs: 1–3 and 11–14 and their fragments, especially the primers according to the invention, are also useful as technical means for performing methods for amplification or modification of a nucleic acid used as a probe, such as:

LCR (Ligase Chain Reaction), described by Landegren et al. in 1988 and improved by Barany et al. in 1991, who employ a thermostable ligase;

RCR (Repair Chain Reaction), described by Segev et al. in 1992;

CPR (Cycling Probe Reaction), described by Duck et al. in 1990; and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic probes according to the present invention are specific to detect a polynucleotide of the invention. By "specific probes" according to the invention is meant any oligonucleotide that hybridizes with one polynucleotide of SEQ ID NOs: 1–3 and 11–14 and which does not hybridize with unrelated sequences. Preferred oligonucleotide probes according to the invention are oligonucleotides I–VI.

In a specific embodiment, the purified polynucleotides according to the present invention encompass polynucleotides having at least 80% homology in their nucleic acid sequences with polynucleotides of SEQ ID NO: 11 to SEQ ID NO: 14, at least 70% identity with SEQ ID NO: 1 to 3. By percentage of nucleotide homology according to the present invention is intended a percentage of identity between the corresponding bases of two homologous polynucleotides, this percentage of identity being purely statistical and the differences between two homologous polynucleotides being located at random and on the whole length of said polynucleotides.

The oligonucleotide probes according to the present invention hybridize specifically with a DNA or RNA molecule comprising all or part of one polynucleotide among SEQ ID NOs: 1–3 and 11–14 under stringent conditions. As an illustrative embodiment, the stringent hybridization conditions used in order to specifically detect a polynucleotide according to the present invention are advantageously the following:

Prehybridization and hybridization are performed at 68° C. in a mixture containing:

5×SSPE (1×SSPE is 0.3 M NaCl, 30 mM tri-sodium citrate

5× Denhardt's solution 0.5% (w/v) sodium dodecyl sulfate (SDS); and

100 $\mu$g ml$^{-1}$ salmon sperm DNA

The washings are performed as follows:

Two washings at laboratory temperature for 10 min. in the presence of 2×SSPE and 0.1% SDS;

One washing at 68° C. for 15 min. in the presence of 1×SSPE, 0.1% SDS; and

One washing at 68° C. for 15 min. in the presence of 0.1×SSPE and 0.1% SDS.

The non-labeled polynucleotides or oligonucleotides of the invention can be directly used as probes. Nevertheless, the polynucleotides or oligonucleotides are generally labeled with a radioactive element ($^{32}$p, $^{35}$S, $^{3}$H, $^{125}$I) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No. FR 78 10975 or by Urdea et al. or Sanchez-Pescador et al. 1988.

Other labeling techniques can also be used, such as those described in the French patents 2 422 956 and 2 518 755. The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the present invention, the probes described herein can be used as "capture probes", and are for this purpose immobilized on a substrate in order to capture the target nucleic acid contained in a biological sample. The captured target nucleic acid is subsequently detected with a second probe, which recognizes a sequence of the target nucleic acid that is different from the sequence recognized by the capture probe.

The oligonucleotide fragments useful as probes or primers according to the present invention can be prepared by cleavage of the polynucleotides of SEQ ID NOs: 1–3 and 11–14 by restriction enzymes, as described in Sambrook et al. in 1989. Another appropriate preparation process of the nucleic acids of the invention containing at most 200 nucleotides (or 200 bp if these molecules are double-stranded) comprises the following steps:

synthesizing DNA using the automated method of beta-cyanethylphosphoramidite described in 1986;

cloning the thus obtained nucleic acids in an appropriate vector; and purifying the nucleic acid by hybridizing to an appropriate probe according to the present invention.

A chemical method for producing the nucleic acids according to the invention, which have a length of more than 200 nucleotides (or 200 bp if these molecules are double-stranded), comprises the following steps:

Assembling the chemically synthesized oligonucleotides having different restriction sites at each end;

cloning the thus obtained nucleic acids in an appropriate vector; and purifying the nucleic acid by hybridizing to an appropriate probe according to the present invention.

The oligonucleotide probes according to the present invention can also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in the European patent application No. 0 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The present invention also pertains to a family of recombinant plasmids containing at least a nucleic acid according to the invention. According to an advantageous embodiment, a recombinant plasmid comprises a polynucleotide of SEQ ID NOs: 1–3 and 11–14 or one nucleic fragment thereof. More specifically, the following plasmids are part of the invention: pIP1633 and pIP1714.

The present invention is also directed to the full length coding sequences of the vgab, vgbB, and vatC genes from *Staphylococci* that are available using the purified polynucleotides according to the present invention, as well as to the polypeptide enzymes encoded by these full length coding sequences. In a specific embodiment of the present invention, the full length coding sequences of the vgaB, vgbB, and vatC genes are isolated from a plasmid or cosmid library of the genome of *Staphylococci* that have been screened with the oligonucleotide probes according to the present invention. The selected positive plasmid or cosmid clones hybridizing with the oligonucleotide probes of the invention are then sequenced in order to characterize the corresponding full length coding sequence, and the DNA insert of interest is then cloned in an expression vector in order to produce the corresponding ATP binding motif conferring resistance to streptogramin A and related compounds, acetyltransferase conferring resistance to streptogramin A and related compounds, or lactonase conferring resistance to streptogramin B and related compounds.

A suitable vector for the expression in bacteria and in particular in *E. coli*, is the pQE-30 vector (QIAexpress) that allows the production of a recombinant protein containing a 6×His affinity tag. The 6×His tag is placed at the C-terminus of the recombinant polypeptide ATP binding motif conferring resistance to streptogramin A and related compounds, acetyltransferase conferring resistance to streptogramin A and related compounds or lactonase conferring resistance to streptogramin B and related compounds, which allows a subsequent efficient purification of the recombinant polypeptide ATP binding motif conferring resistance to streptogramin A and related compounds, acetyltransferase conferring resistance to streptogramin A and related compounds, or lactonase conferring resistance to streptogramin B and related compounds by passage onto a nickel or copper affinity chromatography column. The nickel chromatography column can contain the Ni-NTA resin (Porath et al. 1975).

The polypeptides according to the invention can also be prepared by conventional methods of chemical synthesis, either in a homogenous solution or in solid phase. As an illustrative embodiment of such chemical polypeptide synthesis techniques the homogenous solution technique described by Houbenweyl in 1974 may be cited.

The polypeptides according to the invention can be characterized by binding onto an immunoaffinity chromatography column on which polyclonal or monoclonal antibodies directed to a polypeptide among the ATP binding motif conferring resistance to streptogramin A and related compounds, acetyltransferase conferring resistance to streptogramin A and related compounds, or lactonase conferring resistance to streptogramin B and related compounds of the invention have previously been immobilized.

Another object of the present invention comprises a polypeptide produced by the genetic engineering techniques or a polypeptide synthesized chemically as above described.

The polypeptide ATP binding motif conferring resistance to streptogramin A and related compounds, acetyltransferase conferring resistance to streptogramin A and related compounds, or lactonase conferring resistance to streptogramin B and related compounds according to the present invention are useful for the preparation of polyclonal or monoclonal antibodies that recognize the polypeptides or fragments thereof. The monoclonal antibodies can be prepared from hybridomas according to the technique described by Kohler and Milstein in 1975. The polyclonal antibodies can be prepared by immunization of a mammal, especially a mouse or a rabbit, with a polypeptide according to the invention that is combined with an adjuvant, and then by purifying specific antibodies contained in the serum of the immunized animal on a affinity chromatography column on which has previously been immobilized the polypeptide that has been used as the antigen.

Consequently, the invention is also directed to a method for detecting specifically the presence of a polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:

a polyclonal or monoclonal antibody as described above, optionally labeled; and a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

Indeed, the monoclonal or polyclonal antibodies according to the present invention are useful as detection means in order to identify or characterize a *Staphylococcal* strain carrying genes encoding resistance to streptogramin A or streptogramin B.

The invention also pertains to:

A purified polypeptide or a peptide fragment having at least 10 amino acids, which is recognized by antibodies directed against a polynucleotide sequence conferring resistance to streptogramin and related compounds, corresponding to a polynucleotide sequence according to the invention.

A polynucleotide comprising the full length coding sequence of a *Staphylococcus* streptogramin A and/or B resistant gene containing a polynucleotide sequence according to the invention.

A monoclonal or polyclonal antibody directed against a polypeptide or a peptide fragment encoded by the polynucleotide sequences according to the invention.

A method of detecting the presence of bacterium harboring the polynucleotide sequences according to the invention in a biological sample comprising:
  a) contacting bacterial DNA of the biological sample with a primer or a probe according to the invention, which hybridizes with a nucleotide sequence encoding resistance to streptogramins;
  b) amplifying the nucleotide sequence using said primer or said probe; and
  c) detecting the hybridized complex formed between said primer or probe with the DNA.

A kit for detecting the presence of bacterium having resistance to streptogramin A and/or streptogramin B and harboring the polynucleotide sequences according to the invention in a biological sample, said kit comprising:
  a) a polynucleotide probe according to the invention; and
  b) reagents necessary to perform a nucleic acid hybridization reaction.

A kit for detecting the presence of bacterium having resistance to streptogramin A and harboring the polynucleotide sequences according to the invention in a biological sample, said kit comprising:
  a) a polynucleotide probe according to the invention; and
  b) reagents necessary to perform a nucleic acid hybridization reaction.

A method of screening active antibiotics for the treatment of the infections due to Gram-positive bacteria, comprising the steps of:
  a) bringing into contact a Gram-positive bacteria having a resistance to streptogramin A or streptogramin B and related compounds and containing the polynucleotide sequences according to the invention with the antibiotic; and
  b) measuring an activity of the antibiotic on the bacteria having a resistance to streptogramins and related compounds.

A method of screening for active synthetic molecules capable of penetrating into a bacteria of the family of *staphylococci*, wherein the inhibiting activity of these molecules is tested on at least a polypeptide encoded by the polynucleotide sequences according to the invention comprising the steps of:
  a) contacting a sample of said active molecules with the bacteria;
  b) testing the capacity of the active molecules to penetrate into the bacteria and the capacity of inhibiting a bacterial culture at various concentration of the molecules; and
  c) choosing the active molecule that provides an inhibitory effect of at least 80% on the bacterial culture compared to an untreated culture.

An in vitro method of screening for active molecules capable of inhibiting a polypeptide encoded by the polynucleotide sequences according to the invention, wherein the inhibiting activity of these molecules is tested on at least said polypeptide, said method comprising the steps of:
  a) extracting a purified polypeptide according to the invention;
  b) contacting the active molecules with said purified polypeptide;
  c) testing the capacity of the active molecules, at various concentrations, to inhibit the activity of the purified polypeptide; and
  d) choosing the active molecule that provides an inhibitory effect of at least 80% on the activity of the said purified polypeptide.

A composition of a polynucleotide sequence encoding resistance to streptogramins and related compounds, or inducing resistance in Gram-positive bacteria, wherein said composition comprises a nucleotide sequence corresponding to the resistance phenotype of the plasmid pIP1633 deposited with the C.N.C.M. under the Accession No. I-1768 and of the plasmid pIP1680 deposited with the C.N.C.M. under the Accession No. I-1767 and of the plasmid pIP1714 deposited with the C.N.C.M. under the number I-1877 on Jun. 18, 1997.

A method of detecting the presence of bacterium harboring the polynucleotide sequences according to the invention in a biological sample, said method comprising the steps of:
  a) contacting said sample with an antibody according to the invention that recognizes a polypeptide encoded by said polynucleotide sequences; and
  b) detecting said complex.

A diagnostic kit for in vitro detecting the presence of bacterium harboring the polynucleotide sequences according to the invention in a biological sample, said kit comprising:
  a) a predetermined quantity of monoclonal or polyclonal antibodies according to the invention;
  b) reagents necessary to perform an immunological reaction between the antibodies and a polypeptide encoded by said polynucleotide sequences; and
  c) reagents necessary for detecting said complex between the antibodies and the polypeptide encoded by said polynucleotide sequences.

The inhibiting activity of the molecules can be readily evaluated by one skilled in the art. For example, the inhibiting activity of Vga B can be tested by detecting its ATP hydrolysis as described in J. I. Ross et al. (1990), Mol. Microbiol. 4(7):1207–1214 regarding the rate evaluation of the active efflux of antibiotics from a cell. Ross et al. use a different gene, but their gene product functions as a drug efflux pump in the same way as Vga B does.

The inhibiting activity of Vat C can be tested by visualizing the acetylation reaction as described in Allignet et al. (1993) regarding the mechanism of inactivation of A-type compounds conferred by plasmids pIP680 and pIP1156 by thick layer chromatography and NMR.

The inhibiting activity of Vgb B can be tested by detecting the degradation of streptogramin B or a related compound by a microbiological test as described in Allignet et al. (1988).

Plasmids containing the polynucleotides from *Staphylococci*, which confer streptogramin A and/or B resistance, are referred to herein by the following accession numbers:

| Plasmid | Accession No. |
|---------|---------------|
| pIP1714 | I-1877 |
| pIP1633 | I-1768 |
| pIP680  | I-1767 | and they have been inserted into vectors which have been deposited at the Collection Nationale de Cultures de Microorganismes ("C.N.C.M.") Institut Pasteur, 28, rue du Docteur Roux, F-75724 Paris Cedex 15, France on Jun. 18, 1997, and Aug. 7, 1996, respectively.

EXAMPLES

Example 1

Cloning of the vgaB Gene Carried by Plasmid pIP1633 pIP1633 was isolated from a *S. aureus* transconjugant strain, BM12235, obtained from the donor wild-type *S. aureus* strain, BM3385 (Allignet and El Solh, 1995). This plasmid carried the vatB gene located on a 5.5 BglII fragment, but the other described streptogramin A resistant (SgA$^r$) genes were not detected either by hybridization experiments or by PCR (Allignet and EI Solh, 1995). Since the gene vga was carried by all the tested *staphylococcal* plasmids containing the vat gene (Allignet et al., 1996), the presence of a vga-related gene was suspected in pIP1633. We therefore searched this gene in the recombinant plasmid, pIP1675 (FIG. 1A), containing the vatB-5.5 BglII fragment of pIP1633.

First, the 2.4 kb HindIII-HaeIII fragment of pIP1675, which contains only 10 nucleotide from vatB, was inserted into plasmid pOX300, and the recombinant plasmid, pIP1717 (FIG. 1B), was introduced by electroporation into the *S. aureus* recipient, RN4220 (Kreiswirth et al., 1983). Plasmid pOX300, also named pOX7, (Dyke and Curnock, 1989), is a hybrid of pUC18 and pE194ts and replicates in *E. coli* where it confers resistance to ampicillin and to erythromycin, and in *S. aureus* where only resistance to erythromycin is expressed. The *S. aureus* transformants selected on 10 µg/ml erythromycin were resistant to streptogramin A and related compounds (PIIA MICs=8–16 µg/ml). Thus, the 2.4-kb HindIII-HaeIII insert of pIP1717 (FIG. 1B) probably carried a streptogramin A resistance gene and was sequenced. The nucleotide (nucleotide) sequence of this fragment was determined by the dideoxy method (Sanger et al., 1977) with the reagents and the procedure recommended by the suppliers of the T$^7$ sequencing kit (Pharmacia International). Arrows indicate the direction and extent of each dideoxy-sequencing reaction. (FIG. 1B).

Example 2

The Nucleotide Sequence of the vgaB Gene

Figure 2A:
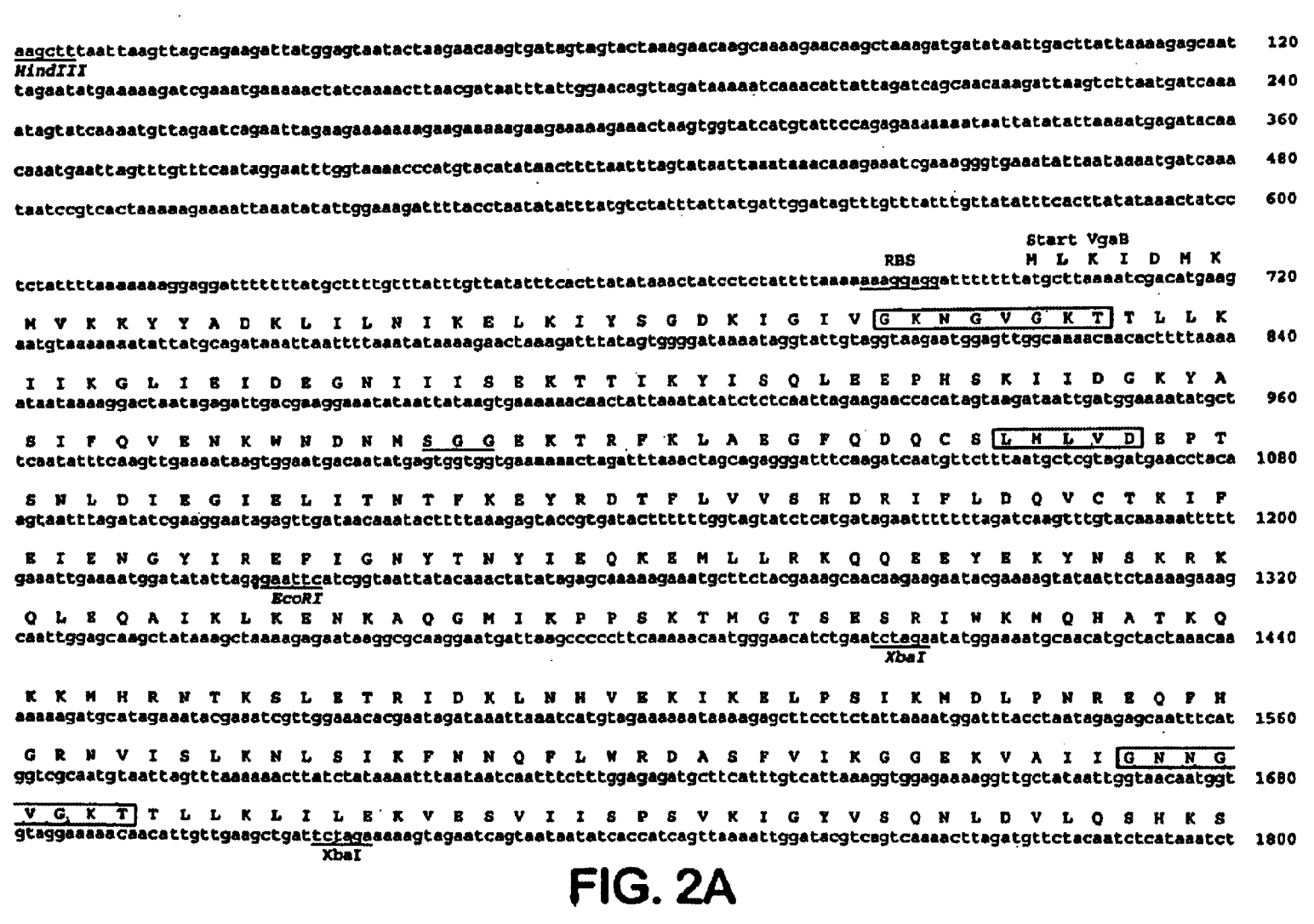
Figure 2B:
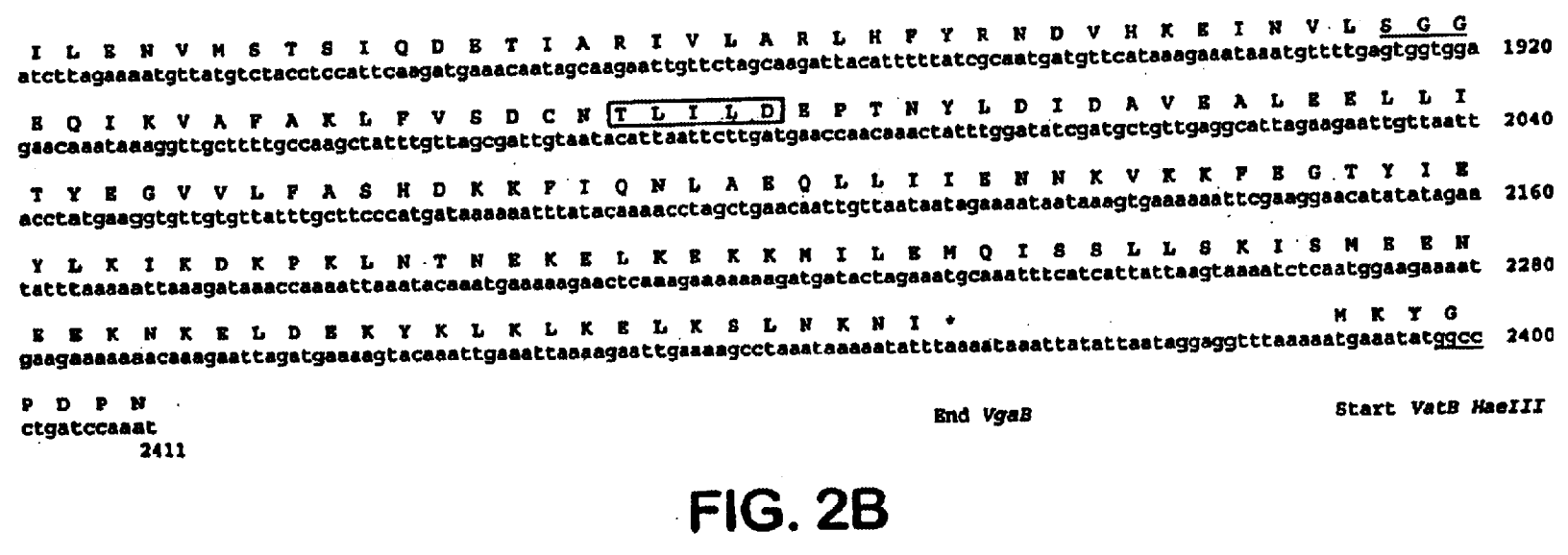

The strategy of sequencing on both strands is outlined in FIG. 1 and the sequence of the 2411-bp HindIII-HaeIII insert is given in FIG. 2. An open reading frame (ORF) of 1674 nucleotide extending from nucleotide 682 to 2356 was detected on the same strand as vatB (FIG. 2). The 1674 nucleotide ORF contained an ATG start codon at nucleotide 700 to 702 and was preceded by an 8 nucleotide putative RBS. The ΔG (free energy of association) of interaction of the most stable structure between this putative RBS and the 3'-terminus of the 16S rRNA (MacLaughlin et al., 1981; Moran et al., 1982) calculated according to Tinoco et al. (1973) was −79.4 kJ/mol. The sequence located between the ATG codon and the TAA stop codon at nucleotide 2356 to 2358 may encode a 552 amino acid protein of 61,327 daltons (Da). This putative gene, named vgaB, had 58.8% nucleotide identity with the 1572 bp gene, vga (Allignet et al., 1992). The G+C content of vgaB (27.2%) is similar to that of vga (29%), but both values are slightly lower than those of the *staphylococcal* genome (32 to 36%) (Kloos and Schleifer, 1986). The nucleotide sequence of vgaB has been submitted to the GenBank/EMBL data bank under accession no. u82085.

Example 3

Amino Acid Sequence Analysis of VgaB

The predicted translation product of the vgaB gene, VgaB, has a calculated isoelectric point (pI) of 9.60. The hydropathy plot of the VgaB sequence according to the algorithm of Kyte and Doolittle (1982) indicates the protein to be hydrophilic. No similarity to known signal sequences of secreted proteins (von Heijne, 1986; Watson, 1984) was observed.

The amino acid sequence of VgaB was compared with the sequences available in databases (GenBank, release 97.0; EMBL, release 48; SwissProt, release 34). Significant similarity to the ATP-binding domains of numerous ATP-binding Cassette (ABC) proteins was found. The protein giving the best match was Vga (48.3% identical amino acid, 70.4% similar amino acid). VgaB and Vga each contain two ATP-binding domains sharing 38.8% and 39.1% identical amino acid, respectively. Each of these domains includes the two ATP-binding motifs described by Walker et al. (1982) (FIG. 2). Moreover, the highly conserved SGG sequence of loop 3 found between the two ATP-binding motifs of all investigated ATP-binding proteins (Barrasa et al., 1995; Hyde et al., 1990) was detected in Vga (Allignet et al., 1992) and VgaB (FIG. 2). According to the predicted tertiary structure of ABC model cassette, this loop would be conveniently located to interact with the cell membrane (Hyde et al., 1990). The inter-ATP-binding domain of VgaB is more rich in glutamine (11 Q in 155 amino acid total) than the rest of the sequence of the protein (11 Q/397 amino acid). In contrast, the proportion of glutamine in the inter-ATP-binding domain of Vga is similar to that in the other part of the protein (4 Q/156 amino acid and 14 Q/366 amino acid, respectively). Neither Vga nor VgaB contains hydrophobic transmembrane domains.

The ABC protein MsrA (Ross et al., 1990) is the most similar to Vga and VgaB (35.2% and 34.4% identical amino acid, respectively). MsrA confers resistance to erythromycin by increasing the efflux of this antibiotic and to streptogramin B by a mechanism not yet elucidated. MsrA contains two ATP-binding domains with 31.8% amino acid identity and separated by a Q-linker, but no hydrophobic stretches that might be potential membrane spanning domains. The hydrophobic proteins, which are expected to interact with MsrA, are those encoded by similar genes mapping near MsrA in two *staphylococcal* strains (smpA, smpB) and also those on the chromosome of the *S. aureus* recipient strain, RN4220 (smpC), which does not carry msrA (Ross et al., 1995). Ross et al. (1996) have recently reported that SmpC found in the chromosome of RN4220 is not essential for the expression of resistance to erythromycin conferred by MsrA. Thus, further experiments are required to elucidate the mechanisms of resistance conferred by msrA, vga, or vgaB genes.

Several ABC transporters, which do not have alternating hydrophobic domains, have been grouped in a subfamily in order to distinguish them from the members of the $ABC_2$ transporter subfamily, the members of which contain hydrophobic transmembrane domains (Barrasa et al., 1995; Olano et al., 1995; Peschke et al., 1995). Thus, VgaB may be considered as a new member of the former ABC transporter subfamily. Excluding VgaB, Vga, and MsrA, most of the known ABC transporters that contain two ATP-binding cassettes but no hydrophobic domain(s) were found in antibiotic or antibiotic producing microorganisms in which they are involved in the active excretion of these molecules. These transporters are encoded by the following genes: ardl, an amino-acylnucleoside antibiotic resistance gene from *Streptomyces capreolus* (Barrasa et al., 1995); carA, a carbomycin-resistance gene from *Streptomyces thermotolerans* (Schoner et al., 1992); ImrC, a lincomycin-resistance gene from *Streptomyces lincolnensis* (Peschke et al., 1995); oleB, an oleandomycin-resistance gene from *Streptomyces antibioticus* (Olano et al., 1995); srmB, a spiramycin-resistance gene from *Streptomyces ambofaciens* (Geistlich et al., 1992); tlrC, a tylosin-resistance gene from *Streptomyces fradiae* (Rosteck et al., 1991); and petT, a pep5 epidermin-resistance gene from *Staphylococcus epidermidis* (Meyer et al., 1995). The amino acid identity between each of these latter ABC transporters and VgaB is between 23.6% and 28.7%.

Degenerate primers designed from an analysis of the alignment of the amino acid sequence of Vga and VgaB may be helpful to detect such putative genes by PCR experiments. In the streptogramins producers, the described resistance to these antibiotics consists of streptogramin A inactivation by an as yet unknown mechanism (Fierro et al., 1989), streptogramin B inactivation by a lactonase (Kim et al., 1974) and putative increased export of streptogramin A and streptogramin B by an integral membrane protein, Ptr, exploiting transmembrane proton gradients (Blanc et al., 1995). The NMR spectra of the modified A compounds may be analyzed to verify if their inactivation in the antibiotic producers is similar to that due to the proteins Vat or VatB, which transfer an o-acetyl group to position C14 of PIIA (Allignet et al., 1993). Interestingly, the *staphylococcal* gene vgb (Allignet et al., 1988) found in most plasmids carrying vga and vat (Allignet et al., 1996), encodes a protein inactivating streptogramin B and related compounds by cleavage of the lactone ring.

Example 4

Distribution and Location of the vgaB Gene in 52 SgA$^R$ and Independent Wild-type *Staphylococci*

A recombinant plasmid containing a fragment of vgaB, pIP1705, was constructed to serve as a probe in hybridization experiments under stringent conditions as described previously (Allignet et al., 1996). pIP1705 consists of pUC19 cleaved with SalI and PstI, and an insert of 1051 bp amplified from within vgaB by the following primers, which introduce PstI or SalI sites:

```
Oligo I
5'-AAGTCGACTGACAATATGAGTGGTGG-3'
       SalI

Oligo II
5'-CTGCAGATGCCTCAACAGCATCGATATCC-3'
      PstI
```

The 52 SgA$^r$ staphylococci investigated (Allignet et al., 1996; El Solh et al., 1980; Loncle et al., 1993) included 10 strains (7 *S. aureus*, 1 *S. simulans*, 1 *S. haemolyticus*, and 1 *S. cohnii urealyticum*), which harbored 26 to 45 kb plasmids containing vga, vat, and vgb; 21 strains (20 *S. aureus* and one *S. epidermidis*), which harbored 50 to 90 kb plasmids containing vatB; 16 strains (12 *S. epidermidis*, three *S. haemolyticus* and one *S. aureus*) with 6 to 15 kb plasmids containing vga; one *S. epidermidis* strain which harbored a plasmid of approximately 20 kb containing vga-vat; and four *S. aureus* strains, which do not carry nucleotide sequences hybridizing with vat, vatB, vga, or vgb. Nucleotide sequences hybridizing with pIP1705 were found only in the 21 large plasmids containing vatB. In all these 21 plasmids including pIP1633, the hybridizing nucleotide sequences were detected on a 1.5 kb EcoRI fragment, which also hybridized with vatB, suggesting that vgaB and vatB have conserved relative positions.

Example 5

Results Concerning vatC and vgbB Genes

The *Staphylococcus cohnii* strain, BM10711, resistant to the synergistic mixtures streptogramin A and streptogramin B and related compounds (pristinamycin, virginiamycin, synergistin, mikamycin, Quinupristin-Dalfopristin) was analyzed. This strain was isolated at Douera hospital (Algeria) where the pristinamycin was frequently used topically. The strain was isolated (Liassin et al., 1997) from a sample provided from a cupboard located in a room occupied by patients suffering from chronic osteomyelitis.

The strain BM10711 harbored several plasmids including pIP1714 (5 kb). This plasmid was isolated by electroporation in a *S. aureus* recipient strain, RN4220. The transformant, harboring pIP1714, was selected on BHIA containing 10 µg/ml pristinamycin IIA. Plasmid pIP1714 conferred resistances to streptogramin A and streptogramin B and related compounds.

Plasmid pIP1714 was linearized by cleavage with HindIII and cloned in the HindIII site of the vector pOX7 also named pOX300 (Dyke et al., 1989, FEMS Microbiol. Lett. 58:209–216). pOX7 results from the cointegration of the *E. coli* vector, pUC18, and *S. aureus* plasmid, pE194. The recombinant plasmid pIP1715 consisting of pOX7 and pIP1714 was used to sequence pIP1714 in its entirety. The gene vatC (636 nucleotides) encoding an acetyltransferase inactivating streptogramin A and related compounds and the gene vgbB (885 nucleotides) encoding a lactonase inactivating streptogramin B and related compounds were found to be carried by this plasmid. The gene vatC had 71.7, 62.2 and 64.1% nucleotides identity with vat-related gene, vatB and satA respectively and the gene vgbB presents 69.5% nucleotides identity with the gene vgb.

VatC acetyltransferase exhibits significant similarity with acetyltransferases having the same enzymatic activity and encoded by the genes vatC, vatB, and sat (respectively 69.8, 58.2 and 66.0% amino acids identity). These proteins belong to a family of xenobiotic acetyltransferases modifying various substrates including streptogramin A and related antibiotics. VgbB lactonase exhibits as well significant similarity with Vgb inactivating streptogramin B and related (67.0% amino acids identity).

The two other genes carried by pIP1714 are pre and repB, encoding proteins involved in mobilization and replication, respectively. These two genes are homologous to those carried by the *staphylococcal* plasmid, pUB110 (McKenzie et al., 1986, Plasmid 15:93–103). Moreover, as reported in FIG. 5, the intergenic sequences of pIP1714 delimited by vatC and repB also exhibited significant similarities with pUB110.

Example 6

Plasmid DNA Isolation from PIIA$^R$ *Staphylococci*

The *staphylococci* were grown after overnight incubation at 37° C. in 200 ml BHI containing 10 μg/ml of PIIA. After 15 min centrifugation at 8000 rpm, the pellet was resuspended in 25 ml TES (Tris 50 mM, EDTA 1 mM, saccharose 7%). After adding 150 μg of lysostaphin, the mixture was incubated 30 min at 37° C. Then, 2 ml of SDS 20% and 6 ml of EDTA.0.25 M were added and the suspension was incubated 15 min at 37° C. 8 ml of NaCl 5M were added and the mixture was kept 90 min at +4° C. After 30 min centrifugation at 8000 rpm, the supernatent was incubated 15 min at 37° C. with 5 μg of Rnase (Boehringer). 10 μg of Proteinase K were added and the suspension was incubated 15 min at 65° C. DNA was precipitated using isopropanol (0.6 V for 1 V of DNA solution). After 30 min centrifugation at 8000 g, the pellet was washed with 10 ml ethanol 70%. The washed DNA was dried at 56° C., dissolved in 10 ml water and purified by dye-buoyant density centrifugation (ethidium bromide-cesium chloride). The extrachromosomal band was collected. After removing ethidium bromide, the solution of plasmid DNA was dialyzed using TE buffer (Tris, 10 mM, EDTA 1 mM, pH 7).

Example 7

Plasmid DNA Isolation from *E. coli*

Cf. QIAfilter™ plasmid maxi protocol for large-scale preparations and QIAprep Spin plasmid kit protocol for mini-preparations.

QIAGEN® GmbH and QIAGEN® Inc. (Hilden, Germany)

Plasmid maxi kit Ref: 12262

Miniprep kit Ref: 27104

Example 8

Transformation by Electroporation of the *S. aureus* Recipient Strain, RN4220

1—Preparation of Cells 200 ml of BHI was inoculated with 20 ml of an overnight culture of RN4220 (Kreiswirth et al., *Nature* 1983, 306:709–712) and incubated at 37° C. with shaking. When the OD reached 0.4 at 600 nm, the suspension was kept in ice. The pellet was washed three times with 20 ml of cold Hepes buffer (saccharose 9.31%—Hepes 0.19%—pH. 7.4). The pellet was resuspended in 2.5 ml of Hepes buffer containing 10% glycerol. Aliquots of 100 μl cell suspension ($3.10^{10}$/ml) were stored at −80° C.

2—Electroporation

After thawing at room temperature, the 100 μl aliquot of cells was kept in ice. After adding 10 μl of a solution containing 1 μg of plasmid DNA, the mixture was transferred to a cold 0.2 cm electroporation cuvette. The GENE PULSER® (BioRad) was set at 25 uF and 2.5 KV and the Pulse Controller to 100 Ω. This produced a pulse with a constant time of 2.3 to 2.5 m sec. The cuvette was removed from the chamber and 1 ml of SOC (2% bactotryptone, 0.5% bactoyeast extract, 10 mM NaCl, 2.5 mMKCl, 10 mM $MgCl_2$, 10 mM $MgSO_4$, 20 mM glucose) was added. The cell suspension was transferred in a propylene tube and incubated with shaking at 37° C. for 1 hr. The suspension was then plated on selective medium, which consisted of BHIA containing 10 μg/ml erythromycin or 10 μg/ml of PIIA. The plates were incubated 48 h at 37° C. and the transformants isolated on selective medium. The further studies were carried out on a single isolated colony.

Example 9

Polymerase Chain Reaction

DNA was amplified by PCR in a Crocodile 11 thermal cycler (Appligene) with approximately 10 ng of cellular DNA or 1 ng of plasmid DNA. The reaction mixture contained 0.6 μM of each oligonucleotide serving as primer, 200 μM of each deoxynucleotide triphosphate, 2.5 U of Taq DNA Polymerase (Amersham, Int.), and 1× buffer (Amersham, Int.). The final reaction volume was adjusted to 100 μl with $H_2O$ and the sample was then covered by 50 μl of heavy white mineral oil (Sigma Chemical Co, St. Louis, Mo.).

PCR experiments were carried out at high or low stringency, depending on the primers used. At high stringency, the PCR was performed with a precycle of 3 min at 95° C. and 2 min at 60° C., 30 cycles of 20 sec at 72° C., 20 sec at 95° C., 20 sec at 60° C. followed by a cycle of 1 min at 72° C. At low stringency, the PCR was performed with a precycle of 5 min at 95° C., 35 cycles of 2 min at 40° C., 1 min 30 sec at 72° C., 30 sec at 95° C. followed by a cycle of 4 min at 40° C. and 12 min at 72° C. The oligonucleotides used at high stringency are indicated in the Table below.

|  |  | PRIMER |
| --- | --- | --- |
| vgaB | Oligo I | 5'-AA<u>GTCGAC</u>TGACAkTATGAGTGGTGG-3'<br>SalI<br>SEQ ID NO.: 15 |
|  | Oligo II | 5'-<u>CTGCAG</u>ATGCCTCAACAGCATCGATATCC-3'<br>PstI<br>SEQ ID NO.: 16 |
| vatC | Oligo III | 5'-AT<u>GAATTC</u>GCAAATCAGCAAGG-3'<br>EcoRI<br>SEQ ID NO.: 17 |
|  | Oligo IV | 5'-TCGTCTC<u>GAGCTC</u>TAGGTCC-3'<br>SacI<br>SEQ ID NO.: 18 |
| vgbB | Oligo V | 5'-CAGCAG<u>TCTAGA</u>TCAGAGTGG-3'<br>XbaI<br>SEQ ID NO.: 19 |
|  | Oligo VI | 5'-CATAC<u>GGATCC</u>ACCTTTTCC-3'<br>BamH1<br>SEQ ID NO.: 20 |

Example 10

Labelling of DNA Probes

Plasmid DNA was labelled with [α-$^{32}$P]dCTP (110 Tbq $mmol^{-1}$) by the random printing technique using the Megaprime DNA labelling system (Amersham).

Example 11

Blotting and Hybridization

Hybond-N+membranes (Amersham) were used for blotting. DNA was transferred from agarose gels to the membranes by the capillary blotting method of Southern Blotting. DNA was denatured and fixed to the membranes according to the protocol described in the handbook user of Hybond-N+membranes.

Prehybridization and hybridization were done at 68° C. in a mixture containing 5×SSPE (1×SSPE is 0.3 M NaCl, 30 m tri-sodium citrate), 5× Denhardt's solution, 0.5% (w/v) SDS, and 100 µg ml$^{-1}$ salmon sperm DNA. The membranes containing DNA transferred from agarose gels were treated with 10 ng ml$^{-1}$ radiolabeled DNA probe. Washing was started with two successive immersions in 2×SSPE, 0.1% SDS, at room temperature for 10 min, followed by one immersion in 1×SSPE, 0.1% SDS, at 68° C. for 15 min, and finally by one immersion in 0.1×SSPE, 0.1% SDS, at 68° C. for 15 min. The washed blots treated with the radiolabeled probe were exposed to Fuji RX film at −70° C.

Example 12

Nucleotides Sequence Determination

For vatC and vgbB, the sequencing reaction was performed by PCR amplification in a final volume of 20 µl using 500 ng of plasmid DNA, 5–10 pmoles of primer and 9.5 µl of DyeTerminators premix according to Applied Biosystems protocol. After heating to 94° C. for 2 min, the reaction was cycled as the following: 25 cycles of 30 s at 94° C., 30 s at 55° C., and 4 min at 60° C. (9600 thermal cycler Perkin Elmer). Removal of excess of DyeTerminators were performed using Quick Spin columns (Boehringer Mannheim). The samples were dried in a vacuum centrifuge and dissolved with 4 µl of deionized formamide EDTA pH 8.0 (5/1). The samples were loaded onto an Applied Biosystems 373A sequencer and run for 12 h on a 4.5% denaturing acrylamide gel.

Primers used for sequencing the following genes:

- vatC

5'-GAAATGGTTGGGAGAAGCATACC-3'  5'-CAGCAATCGCGCCCGTTTG-3'

5'-AATCGGCAGAATTACAAACG-3'  5'-CGTTCCCAATTTCCGTGTTACC-3'

- vgbB

5'-GTTTCTATGCTGATCTGAATC-3'  5'-GTCGTTTGTAATTCTGCCGATT-3'

5'-GGTCTAAATGGCGATATATGG-3'  5'-TTCGAATTCTTTTATCCTACC-3'

For vgaB, DNA was sequenced according to the instructions provided by the T7Sequencing™ kit from Pharmacia Biotech (Uppsala, Sweden), procedures C and D.

Primers used for sequencing the following genes:

- vgaB

5'-GCTTGGCAAAAGCAACC-3'  5'-TGAATATAGGATAG-3'

5'-TTGGATCAGGGCC-3'  5'-CAATTAGAAGAACCAC-3'

5'-CAATTGTTCAGCTAGG-3'  5'-GAATTCATTCTATGG-3'

5'-TACACCATTGTTACC-3'  5'-CAAGGAATGATTAAGCC-3'

-continued

5'-GATTCAGATGTTCCC-3'  5'-TCATGGTCGCAATG-3'

5'-GTTGCTTTCGTAGAAGC-3'  5'-GTTATGTCATCCTC-3'

5'-GGTTCATCTACGAGC-3'  5'-GGATATCGATGCTG-3'

5'-GCCAACTCCATTC-3'  5'-CCTAGCTGAACAATTG-3'

5'-GAAGGTGCCTGATCC-3'  5'-ATACTAGAAATGC-3'

Example 13

DNA Cloning

Figure 4:
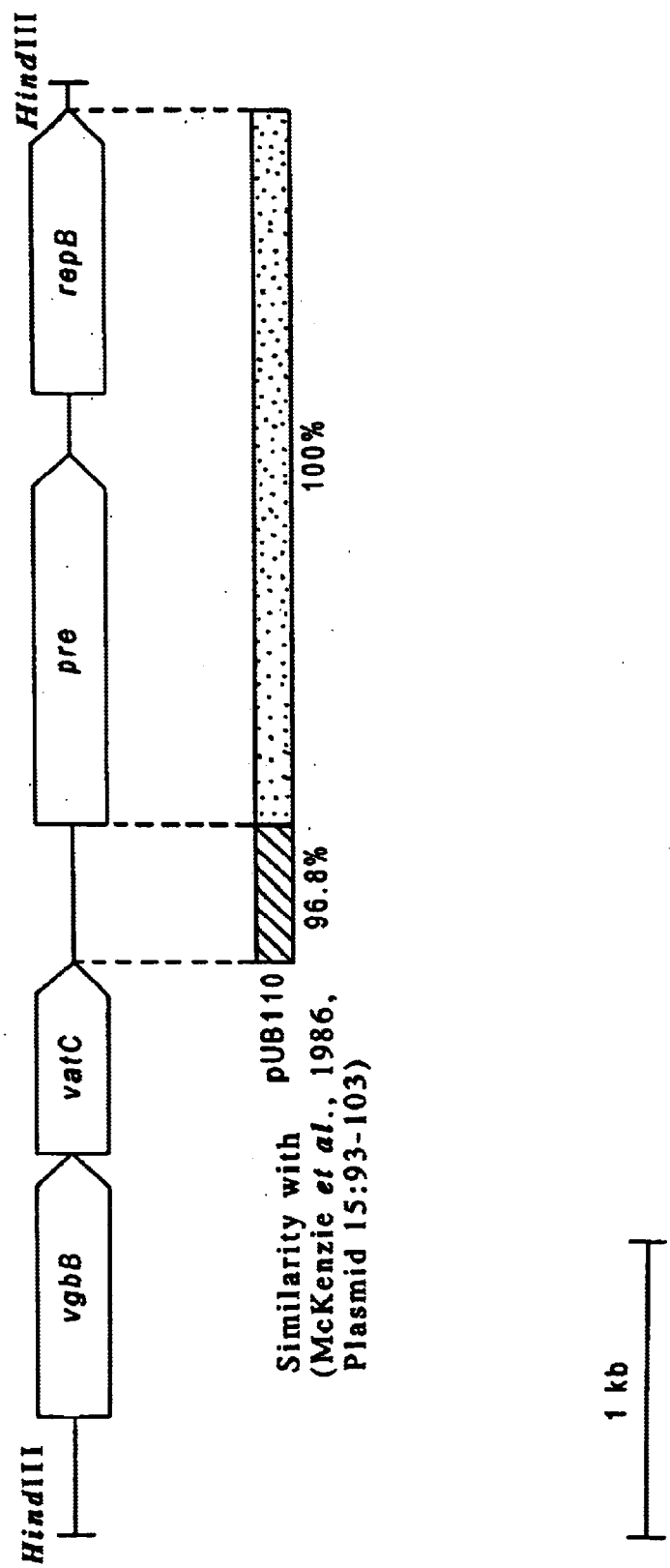
FIG. 4 is a restriction map of the plasmid pIP1714 carrying the genes vatC and vgbB as well as the genes pre and repB of *S. cohnii* strain BM10711 resistant to the synergistic mixtures of streptogramins A and B.

A standard protocol was followed for cloning into the vector pOX7, also named pOX300, the 2.4 kb HindfII-HaeIII fragment of pIP1633 carrying vgaB (FIG. 1) and the plasmid pIP1714 carrying vatC and vgbB (FIG. 4), linearized by cleavage with HindIII. The vector DNA (10–20 µg) and the plasmids used in cloning experiments were cleaved with the appropriate restriction enzymes (30 Units) and purified by GeneClean Kit (Bio 101, La Jolla, Calif.). To avoid religation, the vector cleaved with a single enzyme was dephosphorylated by 30 min incubation at 37° C. with 5 Units of alkaline phosphatase. Ligation was carried out in a total reaction volume of 10 µl containing 0.1 µg of the vector, 0.1 µg of the plasmid, 0.5 mM ATP, 1×T4 DNA ligase buffer and 0.1 Weiss Unit of T4 DNA ligase. After overnight incubation at 16° C., 1 to 2 µl of the ligation mixture are used for transforming competent E. coli and the transformants were selected on solid media containing 100 µg/ml of ampicillin.

Example 14

Susceptibility to Antimicrobial Agents

Susceptibility to antimicrobial agents was determined with a disk diffusion assay and commercially available disks (Diagnostic Pasteur). Additional disks prepared in our laboratory contained streptogramin A (20 µg) or streptogramin B (40 µg).

NCCLS: Performance standards for antimicrobial disk susceptibility test, 1984, Approved standard M2-A3, 4:369–402.

ECCLS: Standard for antimicrobial susceptibility testing by diffusion methods, 1985, ECCLS Document, 5:4-14.

Minimal inhibitory concentrations (MICs) of antibiotics were determined by serial twofold dilutions of antibiotics in MHA (Ericson H. M. and S. C. Sherris, ActaPathol. Microbiol. Scand., 1971, Suppl. 217:Section B).

Despite the relatively low frequency of detection of SgA$^R$ staphylococci (1–10%) (Loncle et al., 1993; Allignet et al., 1996), four genes encoding resistance to streptogramin A have been detected and other resistance gene(s) are suspected to be carried by staphylococci. Surprisingly, the present and previous studies (Allignet et al., 1996) indicate that staphylococcal plasmids carrying two genes encoding streptogramin A resistance by two distinct mechanisms (inactivation by acetyltransferases and increased efflux) are widespread among staphylococci (32 of the 48 plasmids investigated).

References

The following publications have been cited herein. The entire disclosure of each publication is relied upon and incorporated by reference herein.

Allignet, J., Loncle, V., Mazodier, P. and El Solh, N. (1988) Nucleotide sequence of a *staphylococcal* plasmid gene, vgb, encoding a hydrolase inactivating the B components of virginiamycin-like antibiotics. Plasmid 20, 271–275.

Allignet, J., Loncle, V. and El Solh, N. (1992) Sequence of a *staphylococcal* plasmid gene, vga, encoding a putative ATP-binding protein involved in resistance to virginiamycin A-like antibiotics. Gene 117, 45–51.

Allignet, J., Loncle, V., Simenel, C., Delepierre, M. and El Solh, N. (1993) Sequence of a *staphylococcal* gene, vat, encoding an acetyltransferase inactivating the A-type compounds of virginiamycin-like antibiotics. Gene 130, 91–98.

Allignet, J. and El Solh, N. (1995) Diversity among the Gram-positive acetyltransferases inactivating streptogramin A and structurally related compounds, and characterization of a new *staphylococcal* determinant, vatB. Antimicrob. Agents Chemother. 39, 2027–2036.

Allignet, J., Aubert, S., Morvan, A. and El Solh, N. (1996) Distribution of the genes encoding resistance to streptogramin A and related compounds among the *staphylococci* resistant to these antibiotics. Antimicrob. Agents Chemother. 40, 2523–2528.

Allignet, J. and El Solh, N. (1996) Sequence of a *staphylococcal* plasmid gene vga B, encoding a putative ATP-binding protein related to vga involved in resistance to streptogramin A, 8th International Symposium on *Staphylococci* and *Staphylococcal* Infections, 23–26 Jun., 1996, p. 202, 239.

Aumercier, M., Bouhallab, S., Capmau, M. L. and Le Goffic, F. (1992) RP59500: a proposed mechanism for its bactericidal activity. J. Antimicrob. Chemother. 30, 9–14.

Barrasa, M. i., Tercero, J. A., Lacalle, R. A. and Jimenez, A. (1995) The ardl gene from *Streptomyces capreolus* encodes a polypeptide of the ABC-transporters superfamily which confers resistance to the aminonucleotide antibiotic A201A. Eur. J. Biochem. 228, 562–569.

Blanc, V., Salah-Bey, K., Folcher, M. and Thompson, C. J. (1995) Molecular characterization and transcriptional analysis of a multidrug resistance gene cloned from the pristinamycin-producing organism, *Streptomyces pristinaespiralis*. Mol. Microbiol. 17, 989–999.

Cocito, C. (1979) Antibiotics of the virginiamycin family, inhibitors which contain synergistic components. Microbiol. Rev. 43, 145–198.

Di Giambattista, M., Chinali, G. and Cocito, C. (1989) The molecular basis of the inhibitory activities of type A and type B synergimycins and related antibiotics on ribosomes. J. Antimicrob. Chemother. 24, 485–507.

Dyke, K. G. H. and Curnock, S. P. (1989) The nucleotide sequence of a small crypticplasmid found in *Staphylococcus aureus* and its relationship to other plasmids. FEMS Microbiol. Lett. 58, 209–216.

El Solh, N., Fouace, J. M., Shalita, Z., Bouanchaud, D. H., Novick, R. P. and Chabbert, Y. A. (1980) Epidemiological and structural studies of *Staphylococcus aureus* R plasmids mediating resistance to tobramycin and streptogramin. Plasmid 4, 117–120.

Entenza, J. M., Drugeon, H., Glauser, M. P. and Moreillon, P. (1995) Treatment of experimental endocarditis due to erythromycin-susceptible or -resistant methicillin-resistant *Staphylococcus aureus* with RP59500. Antimicrob. Agents Chemother. 39, 1419–1424.

Fantin, B., Leclercq, R., Merl, Y., Saint-Julien, L., Veyrat, C., Duval, J. and Carbon, C. (1995) Critical influence of resistance to streptogramin B-type antibiotics on activity of RP59500 (quinupristin-dalfopristin) in experimental endocarditis due to *hylococcus aureus*. Antimicrob. Agents Chemother. 39, 400–405.

Fierro, J. F., Vilches, C., Hardisson, C. and Salas, J. A. (1989) Streptogramins-inactivating activity in three producer *streptomycetes*. FEMS Microbiol. Lett. 58, 243–246.

Geistlich, M., Losick, R., Turner, J. R. and Rao, R. N. (1992) Characterization of a novel regulatory gene governing the expression of a polyketide synthase gene in *Streptomyces ambofaciens*. Mol. Microbiol. 6, 2019–2029.

Griswold, M. W., Lomaestro, B. M. and Briceland, L. L. (1996) Quinupristin-dalfopristin (RP59500)—an injectable streptogramin combination. Amer. J. Health-Syst. Pharm. 53, 2045–2053.

Hyde, S. C., Emsley, P., Hartshorn, M. J., Mimmack, M. M., Gileadi, U., Pearce, S. R., Gallagher, M. P., Gill, D. R., Hubbard, R. E. and Higgins, C. F. (1990) Structural model of ATP-binding proteins associated with cystic fibrosis, multidrug resistance and bacterial transport. Nature 346, 362–365.

Kim, C. H., Otake, N. and Yonehara, H. (1974) Studies on mikamycin B lactonase.
I. Degradation of mikamycin B by *Streptomyces mitakaensis*. J. Antibiot. 27, 903–908.

Kloos, W. E. and Schleifer, K. H. (1986). Genus IV. *Staphylococcus* Rosenbach 1884. 18AL, (Nom. Cons. ( )pin. 17 Jud. Comm. 1958, 153). In: Sneath, P. H. A., Mair, N. S., Sharpe, M. E. and Holt, J. G. (Eds.), Bergey's manual of systematic bacteriology. Williams & Wilkins, Baltimore, Vol. 2, pp. 1013–103.

Kreiswirth, B. N., Lofdahl, S., Bethey, M. J., O'Reilly, M., Shlievert, P. M., Bergdoll, M. S. and Novick, R. P. (1983) The toxic shock exotoxin structural gene is not detectably transmitted by a prophage. Nature 306, 709–712.

Kyte, J. and Doolittle, R. F. (1982) A simple method for displaying the hydropathic character of a protein. J. Mol. Biol. 157, 105–132.

Liassine, N., Allignet, J. Morvan, A., Aubert, S. and El Solh, N. (1997) Multiplicity of the genes and plasmids conferring resistance to pristinamycin in *Staphylococci* selected in an
Algerian hospital, Zbl. Bakt. 1212.

Loncle, V., Casetta, A., Buu-Ho., A. and El Solh, N. (1993) Analysis of pristinamycin-resistant *Staphylococcus epidermidis* isolates responsible for an outbreak in a parisian hospital. Antimicrob. Agents Chemother. 37, 2159–2165.

MacLaughlin, J. R., Murray, C. L. and Rabinowitz, C. (1981) Unique features in the ribosome binding site sequence of the Gram-positive *Staphylococcus aureus* §-lactamase gene. J. Biol. Chem. 256, 11283–11291.

Meyer, C., Bierbaum, G., Heidrich, C., Reis, M., SŸling, J., Iglesias-Wind, M., Kempter, C., Molitor, E. and Sahl, H. -G. (1995) Nucleotide sequence of the antibiotic Pep5 biosynthetic gene cluster and functional analysis of PepP and PepC: Evidence for a role of PepC in thioether formation. Eur. J. Biochem. 232, 478–489.

Moran, C. P., Jr., Lang, N., LeGrice, S. F. J., Lee, G., Stephens, M., Sonenshein, A. L., Pero, J. and Losick, R.

(1982) Nucleotide sequences that signal the initiation of transcription and translation in *Bacillus subtilis*. Mol. Gen. Genet. 186, 339–346.

Olano, C., Rodriguez, A. M., Mndez, C. and Salas, J. A. (1995) A second ABC transporter is involved in oleandomycin resistance and its secretion by *Streptomyces antibioticus*. Mol. Microbiol. 16, 333–343.

Peschke, U., Schmidt, H., Zhang, H. -Z. and Piepersberg, W. (1995) Molecular characterization of the lincomycin-production gene cluster of *Streptomyces lincolnensis* 78–11. Mol. Microbiol. 16, 1137–1156.

Rende-Fournier, R., Leclercq, R., Galimand, M., Duval, J. and Courvalin, P. (1993) identification of the satA gene encoding a streptogramin A acetyltransferase in *Enterococcus faecium* BM4145. Antimicrob. Agents Chemother. 37, 2119–2125.

Ross, J. I., Eady, E. A., Cove, J. H., Cunliffe, W. J., Baumberg, S. and Wootton, J. C. (1990) Inducible erythromycin resistance in *staphylococci* is encoded by a member of the ATP-binding transport super-gene family. Mol. Microbiol. 4(7), 1207–1214.

Ross, J. I., Eady, E. A., Cove, J. H. and Baumberg, S. (1995) Identification of a chromosomally encoded ABC-transport system with which the *staphylococcal* erythromycin exporter MsrA may interact. Gene 153, 93–98.

Ross, J. I., Eady, E. A., Cove, H. H. and Baumberg, S. (1996) Minimal functional system required for expression of erythromycin resistance by MSRA in *Staphyloocccus aureus* RN4220. Gene 183, 143–148.

Rosteck, P. R. J., Reynolds, P. A. and Hershberger, C. L. (1991) Homology between proteins controlling *Streptomyces fradiae* tylosin resistance and ATP-binding transport. Gene 102, 27–32.

Sanger, F., Nicklen, S. and Coulson, A. R. (1977) DNA sequencing with chain terminating inhibitors. Proc. Natl. Acad. Sci. USA 74, 5463–5467.

Schoner, B., Geistlich, M., Rosteck, P. R., Jr., Rao, R. N., Seno, E., Reynolds, P., Cox, K., Burgett, S. and Hershberger, C. (1992) Sequence similarity between macrolide-resistance determinants and ATP-binding transport proteins. Gene 115, 93–96.

Southern, E. M. (1975) Detection of specific sequences among DNA fragments separated by gel electrophoresis. J. Mol. Biol. 98, 503–517.

Tinoco, I., Jr., Borer, P. N., Dengler, B., Levine, M. D., Uhlenbeck, O. C., Crothers, D. M. and Gralla, J. (1973) Improved estimation of secondary structure in ribonucleic acids. Nature New Biol. 246, 40–41.

Torralba, M. D., Frey, S. E. and Lagging, L. M. (1995) Treatment of methicillin-resistant *Staphylococcus aureus* infection with quinupristin dalfopristin. Clin. Infect. Dis. 21, 460–461.

von Heijne, G. (1986) A new method for predicting signal sequence cleavage sites. Nucl. Acids Res. 14, 4683–4690.

Walker, J. E., Saraste, M., Runswick, M. J. and Gay, N. J. (1982) Distantly related sequences in the a- and §-subunits of ATP synthase, myosin, kinases and other ATP-requiring enzymes and a common nucleotide binding fold. EMBO J. 1, 945–951.

Watson, M. E. E. (1984) Compilation of published signal sequences. Nucl. Acids Res. 12, 5145–5148.

What is claimed is:

1. A method of detecting a bacterium in a biological sample that harbors at least one polynucleotide selected from the group consisting of:
   i) a polynucleotide comprising the sequence of SEQ ID NO: 1;
   ii) a polynucleotide comprising the sequence of SEQ ID NO: 2; and
   iii) a polynucleotide comprising the sequence of SEQ ID NO: 3, said method comprising:
   a) contacting bacterial DNA of the biological sample with a primer or a probe comprising at least 10 nucleotides that hybridizes under stringent conditions to at least one of the polynucleotides i), ii), and iii);
   b) amplifying the polynucleotide sequence using said primer or said probe; and
   c) detecting a hybridized complex formed between said primer or probe and the DNA.

2. A kit for detecting a bacterium that is resistant to a streptogramin and harbors at least one polynucleotide selected from the group consisting of:
   i) a polynucleotide comprising the sequence of SEQ ID NO: 1;

ii) a polynucleotide comprising the sequence of SEQ ID NO: 2; and iii) a polynucleotide comprising the sequence of SEQ ID NO: 3, said kit comprising:

a) a polynucleotide primer or probe comprising at least 10 nucleotides that hybridizes under stringent conditions to at least one of the polynucleotides i), ii), and iii); and b) at least one reagent to perform a nucleic acid hybridization reaction.

3. A kit for detecting a bacterium that is resistant to a streptogramin and harbors at least one of a polynucleotide comprising SEQ ID NO: 12 and a polynucleotide comprising SEQ ID NO: 14, said kit comprising:

a) a polynucleotide primer or probe comprising at least 10 nucleotides that hybridizes under stringent conditions to at least one of a polynucleotide consisting of SEQ ID NO: 12 and a polynucleotide consisting of SEQ ID NO: 14; and b) at least one reagent to perform a nucleic acid hybridization reaction.

4. A method of detecting a bacterium in a biological sample that harbors at least one of a polynucleotide comprising SEQ ID NO: 12 and a polynucleotide comprising SEQ ID NO: 14, said method comprising:

a) contacting bacterial DNA of the biological sample with a polynucleotide primer or probe comprising at least 10 nucleotides that hybridizes under stringent conditions to at least one of a polynucleotide consisting of SEQ ID NO: 12 and a polynucleotide consisting of SEQ ID NO: 14;

b) amplifying the hybridized polynucleotide using said polynucleotide primer or probe; and c) detecting a hybridized complex formed between said polynucleotide primer or probe and the DNA.

5. The method according to claim 1, wherein the polynucleotide primer or probe is selected from the group consisting of SEQ ID NO.: 15, SEQ ID NO.: 16, SEQ ID NO.: 17, SEQ ID NO.: 18, SEQ ID NO.: 19, and SEQ ID NO.: 20.

6. The method according to claim 1, wherein the polynucleotide primer or probe is selected from the group consisting of SEQ ID NO.: 15, SEQ ID NO.: 16, SEQ ID NO.: 17, and SEQ ID NO.: 18.

7. The method according to claim 4, wherein the polynucleotide primer or probe is selected from the group consisting of SEQ ID NO.: 15, SEQ ID NO.: 16, SEQ ID NO.: 17, SEQ ID NO.: 18, SEQ ID NO.: 19, and SEQ ID NO.: 20.

8. The method according to claim 4, wherein the polynucleotide primer or probe is selected from the group consisting of SEQ ID NO.: 15, SEQ ID NO.: 16, SEQ ID NO.: 17, and SEQ ID NO.: 18.

9. The kit according to claim 2, wherein the polynucleotide primer or probe is selected from the group consisting of SEQ ID NO.: 15, SEQ ID NO.: 16, SEQ ID NO.: 17, SEQ ID NO.: 18, SEQ ID NO.: 19, and SEQ ID NO.: 20.

10. The kit according to claim 2, wherein the polynucleotide primer or probe is selected from the group consisting of SEQ ID NO.: 15, SEQ ID NO.: 16, SEQ ID NO.: 17, and SEQ ID NO.: 18.

11. The kit according to claim 3, wherein the polynucleotide primer or probe is selected from the group consisting of SEQ ID NO.: 15, SEQ ID NO.: 16, SEQ ID NO.: 17, SEQ ID NO.: 18, SEQ ID NO.: 19, and SEQ ID NO.: 20.

12. The kit according to claim 3, wherein the polynucleotide primer or probe is selected from the group consisting of SEQ ID NO.: 15, SEQ ID NO.: 16, SEQ ID NO.: 17, and SEQ ID NO.: 18.

13. A method for detecting the presence of microorganisms resistant to streptogramin A and/or streptogramin B in a biological sample, the method comprising:

a) contacting DNA of the biological sample with a polynucleotide primer or probe comprising at least 10 nucleotides that hybridizes under stringent conditions to at least one of SEQ ID NO: 1; SEQ ID NO: 2; SEQ ID NO: 3; SEQ ID NO: 11; SEQ ID NO: 12; SEQ ID NO: 13; and SEQ ID NO: 14; and b) detecting a hybridized complex formed between said polynucleotide primer or probe and the DNA.

* * * * *

UNITED STATES PATENT AND TRADEMARK OFFICE
CERTIFICATE OF CORRECTION

PATENT NO. : 6,936,422 B2
DATED : August 30, 2005
INVENTOR(S) : Névine El Solh et al.

Page 1 of 1

It is certified that error appears in the above-identified patent and that said Letters Patent is hereby corrected as shown below:

<u>Title page,</u>
Item [57], ABSTRACT,
Line 12, "to the polypeptide" should read -- to the polypeptides --.

<u>Column 56,</u>
Line 62, "the DNA" should read -- said bacterial DNA of the biological sample --.

<u>Column 57,</u>
Line 36, "the DNA" should read -- said bacterial DNA of the biological sample --.

<u>Column 58,</u>
Line 37, delete "SEQ ID NO: 11;".
Lines 37-38, delete "SEQ ID NO: 13;".
Line 40, "the DNA" should read -- said DNA of the biological sample --.

Signed and Sealed this

Twenty-second Day of November, 2005

JON W. DUDAS
*Director of the United States Patent and Trademark Office*

SEQUENCE LISTING

<160> NUMBER OF SEQ ID NOS: 50

<210> SEQ ID NO 1
<211> LENGTH: 1656
<212> TYPE: DNA
<213> ORGANISM: Staphyloccocus

<400> SEQUENCE: 1

```
atgcttaaaa tcgacatgaa gaatgtaaaa aaatattatg cagataaatt aattttaaat      60
ataaaagaac taaagattta tagtggggat aaaataggta ttgtaggtaa gaatggagtt     120
ggcaaaacaa cacttttaaa aataataaaa ggactaatag agattgacga aggaaatata     180
attataagtg aaaaaacaac tattaaatat atctctcaat tagaagaacc acatagtaag     240
ataattgatg gaaaatatgc ttcaatattt caagttgaaa ataagtggaa tgacaatatg     300
agtggtggtg aaaaaactag atttaaacta gcagagggat ttcaagatca atgttcttta     360
atgctcgtag atgaacctac aagtaattta gatatcgaag gaatagagtt gataacaaat     420 actttaaag agtaccgtga tactttttg gtagtatctc atgatagaat tttttttagat     480 caagtttgta caaaaatttt tgaaattgaa aatggatata ttagagaatt catcggtaat     540
tatacaaact atatagagca aaaagaaatg cttctacgaa agcaacaaga agaatacgaa     600
aagtataatt ctaaaagaaa gcaattggag caagctataa agctaaaaga gaataaggcg     660
caaggaatga ttaagccccc ttcaaaaaca atgggaacat ctgaatctag aatatggaaa     720
```

```
atgcaacatg ctactaaaca aaaaaagatg catagaaata cgaaatcgtt ggaaacacga      780
atagataaat taaatcatgt agaaaaaata aaagagcttc cttctattaa aatggattta      840
cctaatagag agcaatttca tggtcgcaat gtaattagtt taaaaaactt atctataaaa      900
tttaataatc aatttctttg gagagatgct tcatttgtca ttaaaggtgg agaaaaggtt      960
gctataattg gtaacaatgg tgtaggaaaa acaacattgt tgaagctgat tctagaaaaa     1020
gtagaatcag taataatatc accatcagtt aaaattggat acgtcagtca aaacttagat     1080
gttctacaat ctcataaatc tatcttagaa aatgttatgt ctacctccat tcaagatgaa     1140
acaatagcaa gaattgttct agcaagatta cattttatc gcaatgatgt tcataaagaa      1200
ataaatgttt tgagtggtgg agaacaaata aaggttgctt tgccaagct atttgttagc      1260 gattgtaata cattaattct tgatgaacca acaaactatt tggatatcga tgctgttgag     1320
gcattagaag aattgttaat tacctatgaa ggtgttgtgt atttgcttc ccatgataaa      1380 aaatttatac aaaacctagc tgaacaattg ttaataatag aaaataataa agtgaaaaaa     1440
ttcgaaggaa catatataga atatttaaaa attaaagata aaccaaaatt aaatacaaat     1500
gaaaaagaac tcaaagaaaa aaagatgata ctagaaatgc aaatttcatc attattaagt     1560
aaaatctcaa tggaagaaaa tgaagaaaaa aacaaagaat tagatgaaaa gtacaaattg     1620
aaattaaaag aattgaaaag cctaaataaa aatatt                               1656

<210> SEQ ID NO 2
<211> LENGTH: 636
<212> TYPE: DNA
<213> ORGANISM: Staphyloccocus

<400> SEQUENCE: 2
atgaaatggc aaaatcagca aggccccaat ccagaagaaa tatacccctat agaaggtaat      60 aaacatgttc aatttattaa accatctata acaaagccca atattttagt tggggaatat     120
tcatattacg atagtaaaga tggtgaatct ttttgaaagcc aagttctta tcactatgaa     180 ttgattgggg ataaactaat attagggaag ttttgttcta ttggacccgg aacgacattt     240
ataatgaatg gggctaatca tcgtatggat ggttcaacat ttccattcaa tcttttcgga     300
aatggttggg agaagcatac ccctacattg aagaccttc cttataaggg taacacggaa     360
attgggaacg atgtttggat tggacgagat gtgacaatta tgcccggtgt aaaaatagga     420
aacggggcta ttattgcagc aaaatcggtt gtgacaaaga acgttgatcc ttattcagtt     480
gttggcggta atccttcacg attaattaag ataaggtttt ccaaggaaaa aatcgcagca     540
ttactaaaag taaggtggtg ggacctagag atagagacga taaatgaaaa tattgattgc     600
atcctgaatg gtgatataaa aaaggttaaa agaagt                               636

<210> SEQ ID NO 3
<211> LENGTH: 885
<212> TYPE: DNA
<213> ORGANISM: Staphyloccocus

<400> SEQUENCE: 3
atgaattttt atttagagga gtttaacttg tctattcccg attcaggtcc atacggtata      60
acttcatcag aagacggaaa ggtatggttc acacaacata aggcaaacaa aatcagcagt     120
ctagatcaga gtggtaggat aaaagaattc gaagttccta cccctgatgc taaagtgatg     180
tgtttaattg tatcttcact tggagacata tggtttacag agaatggtgc aaataaaatc     240
ggaaagctct caaaaaaagg tggcttttaca gaatatccat tgccacagcc ggattctggt     300
```

```
ccttacggaa taacggaagg tctaaatggc gatatatggt ttacccaatt gaatggagat    360
cgtataggaa agttgacagc tgatgggact atttatgaat atgatttgcc aaataaggga    420
tcttatcctg cttttattac tttaggttcg gataacgcac tttggttcac ggagaaccaa    480
aataattcta ttggaaggat tacaaataca gggaaattag aagaatatcc tctaccaaca    540
aatgcagcgg ctccagtggg tatcactagt ggtaacgatg gtgcactctg gtttgtcgaa    600
attatgggca acaaaatagg tcgaatcact acaactggtg agattagcga atatgatatt    660
ccaactccaa acgcacgtcc acacgctata accgcgggga aaaatagcga atatggtttt    720
actgaatggg gggcaaatca aatcggcaga attacaaacg acaaaacaat tcaagaatat    780
caacttcaaa cagaaaatgc ggaacctcat ggtattacct ttggaaaaga tggatccgta    840
tggtttgcat taaaatgtaa aattgggaag ctgaatttga acgaa                   885
```

<210> SEQ ID NO 4
<211> LENGTH: 552
<212> TYPE: PRT
<213> ORGANISM: Staphyloccocus

<400> SEQUENCE: 4

```
Met Leu Lys Ile Asp Met Lys Asn Val Lys Lys Tyr Tyr Ala Asp Lys
  1               5                  10                  15

Leu Ile Leu Asn Ile Lys Glu Leu Lys Ile Tyr Ser Gly Asp Lys Ile
             20                  25                  30

Gly Ile Val Gly Lys Asn Gly Val Gly Lys Thr Thr Leu Leu Lys Ile
         35                  40                  45

Ile Lys Gly Leu Ile Glu Ile Asp Glu Gly Asn Ile Ile Ile Ser Glu
     50                  55                  60

Lys Thr Thr Ile Lys Tyr Ile Ser Gln Leu Glu Glu Pro His Ser Lys
 65                  70                  75                  80

Ile Ile Asp Gly Lys Tyr Ala Ser Ile Phe Gln Val Glu Asn Lys Trp
                 85                  90                  95

Asn Asp Asn Met Ser Gly Gly Glu Lys Thr Arg Phe Lys Leu Ala Glu
            100                 105                 110

Gly Phe Gln Asp Gln Cys Ser Leu Met Leu Val Asp Glu Pro Thr Ser
        115                 120                 125

Asn Leu Asp Ile Glu Gly Ile Glu Leu Ile Thr Asn Thr Phe Lys Glu
    130                 135                 140

Tyr Arg Asp Thr Phe Leu Val Val Ser His Asp Arg Ile Phe Leu Asp
145                 150                 155                 160

Gln Val Cys Thr Lys Ile Phe Glu Ile Glu Asn Gly Tyr Ile Arg Glu
                165                 170                 175

Phe Ile Gly Asn Tyr Thr Asn Tyr Ile Glu Gln Lys Glu Met Leu Leu
            180                 185                 190

Arg Lys Gln Gln Glu Glu Tyr Glu Lys Tyr Asn Ser Lys Arg Lys Gln
        195                 200                 205

Leu Glu Gln Ala Ile Lys Leu Lys Glu Asn Lys Ala Gln Gly Met Ile
    210                 215                 220

Lys Pro Pro Ser Lys Thr Met Gly Thr Ser Glu Ser Arg Ile Trp Lys
225                 230                 235                 240

Met Gln His Ala Thr Lys Gln Lys Met His Arg Asn Thr Lys Ser
                245                 250                 255

Leu Glu Thr Arg Ile Asp Lys Leu Asn His Val Glu Lys Ile Lys Glu
            260                 265                 270
```

-continued

```
Leu Pro Ser Ile Lys Met Asp Leu Pro Asn Arg Glu Gln Phe His Gly
            275                 280                 285

Arg Asn Val Ile Ser Leu Lys Asn Leu Ser Ile Lys Phe Asn Asn Gln
        290                 295                 300

Phe Leu Trp Arg Asp Ala Ser Phe Val Ile Lys Gly Gly Glu Lys Val
305                 310                 315                 320

Ala Ile Ile Gly Asn Asn Gly Val Gly Lys Thr Thr Leu Leu Lys Leu
                325                 330                 335

Ile Leu Glu Lys Val Glu Ser Val Ile Ser Pro Ser Val Lys Ile
            340                 345                 350

Gly Tyr Val Ser Gln Asn Leu Asp Val Leu Gln Ser His Lys Ser Ile
        355                 360                 365

Leu Glu Asn Val Met Ser Thr Ser Ile Gln Asp Glu Thr Ile Ala Arg
        370                 375                 380

Ile Val Leu Ala Arg Leu His Phe Tyr Arg Asn Asp Val His Lys Glu
385                 390                 395                 400

Ile Asn Val Leu Ser Gly Gly Glu Gln Ile Lys Val Ala Phe Ala Lys
                405                 410                 415

Leu Phe Val Ser Asp Cys Asn Thr Leu Ile Leu Asp Glu Pro Thr Asn
                420                 425                 430

Tyr Leu Asp Ile Asp Ala Val Glu Ala Leu Glu Leu Leu Ile Thr
            435                 440                 445

Tyr Glu Gly Val Val Leu Phe Ala Ser His Asp Lys Lys Phe Ile Gln
        450                 455                 460

Asn Leu Ala Glu Gln Leu Leu Ile Ile Glu Asn Asn Lys Val Lys Lys
465                 470                 475                 480

Phe Glu Gly Thr Tyr Ile Glu Tyr Leu Lys Ile Lys Asp Lys Pro Lys
                485                 490                 495

Leu Asn Thr Asn Glu Lys Glu Leu Lys Glu Lys Met Ile Leu Glu
        500                 505                 510

Met Gln Ile Ser Ser Leu Leu Ser Lys Ile Ser Met Glu Glu Asn Glu
        515                 520                 525

Glu Lys Asn Lys Glu Leu Asp Glu Lys Tyr Lys Leu Lys Leu Lys Glu
        530                 535                 540

Leu Lys Ser Leu Asn Lys Asn Ile
545                 550

<210> SEQ ID NO 5
<211> LENGTH: 212
<212> TYPE: PRT
<213> ORGANISM: Staphyloccocus

<400> SEQUENCE: 5

Met Lys Trp Gln Asn Gln Gln Gly Pro Asn Pro Glu Glu Ile Tyr Pro
1               5                   10                  15

Ile Glu Gly Asn Lys His Val Gln Phe Ile Lys Pro Ser Ile Thr Lys
            20                  25                  30

Pro Asn Ile Leu Val Gly Glu Tyr Ser Tyr Tyr Asp Ser Lys Asp Gly
        35                  40                  45

Glu Ser Phe Glu Ser Gln Val Leu Tyr His Tyr Glu Leu Ile Gly Asp
    50                  55                  60

Lys Leu Ile Leu Gly Lys Phe Cys Ser Ile Gly Pro Gly Thr Thr Phe
65              70                  75                  80

Ile Met Asn Gly Ala Asn His Arg Met Asp Gly Ser Thr Phe Pro Phe
```

```
                    85                  90                  95
Asn Leu Phe Gly Asn Gly Trp Glu Lys His Thr Pro Thr Leu Glu Asp
            100                 105                 110
Leu Pro Tyr Lys Gly Asn Thr Glu Ile Gly Asn Asp Val Trp Ile Gly
            115                 120                 125
Arg Asp Val Thr Ile Met Pro Gly Val Lys Ile Gly Asn Gly Ala Ile
            130                 135                 140
Ile Ala Ala Lys Ser Val Val Thr Lys Asn Val Asp Pro Tyr Ser Val
145                 150                 155                 160
Val Gly Gly Asn Pro Ser Arg Leu Ile Lys Ile Arg Phe Ser Lys Glu
            165                 170                 175
Lys Ile Ala Ala Leu Leu Lys Val Arg Trp Trp Asp Leu Glu Ile Glu
            180                 185                 190
Thr Ile Asn Glu Asn Ile Asp Cys Ile Leu Asn Gly Asp Ile Lys Lys
            195                 200                 205
Val Lys Arg Ser
        210

<210> SEQ ID NO 6
<211> LENGTH: 295
<212> TYPE: PRT
<213> ORGANISM: Staphyloccocus

<400> SEQUENCE: 6

Met Asn Phe Tyr Leu Glu Glu Phe Asn Leu Ser Ile Pro Asp Ser Gly
1               5                   10                  15
Pro Tyr Gly Ile Thr Ser Ser Glu Asp Gly Lys Val Trp Phe Thr Gln
            20                  25                  30
His Lys Ala Asn Lys Ile Ser Ser Leu Asp Gln Ser Gly Arg Ile Lys
            35                  40                  45
Glu Phe Glu Val Pro Thr Pro Asp Ala Lys Val Met Cys Leu Ile Val
        50                  55                  60
Ser Ser Leu Gly Asp Ile Trp Phe Thr Glu Asn Gly Ala Asn Lys Ile
65                  70                  75                  80
Gly Lys Leu Ser Lys Lys Gly Phe Thr Glu Tyr Pro Leu Pro Gln
            85                  90                  95
Pro Asp Ser Gly Pro Tyr Gly Ile Thr Glu Gly Leu Asn Gly Asp Ile
            100                 105                 110
Trp Phe Thr Gln Leu Asn Gly Asp Arg Ile Gly Lys Leu Thr Ala Asp
            115                 120                 125
Gly Thr Ile Tyr Glu Tyr Asp Leu Pro Asn Lys Gly Ser Tyr Pro Ala
130                 135                 140
Phe Ile Thr Leu Gly Ser Asp Asn Ala Leu Trp Phe Thr Glu Asn Gln
145                 150                 155                 160
Asn Asn Ser Ile Gly Arg Ile Thr Asn Thr Gly Lys Leu Glu Glu Tyr
            165                 170                 175
Pro Leu Pro Thr Asn Ala Ala Pro Val Gly Ile Thr Ser Gly Asn
            180                 185                 190
Asp Gly Ala Leu Trp Phe Val Glu Ile Met Gly Asn Lys Ile Gly Arg
            195                 200                 205
Ile Thr Thr Thr Gly Glu Ile Ser Glu Tyr Asp Ile Pro Thr Pro Asn
        210                 215                 220
Ala Arg Pro His Ala Ile Thr Ala Gly Lys Asn Ser Glu Ile Trp Phe
225                 230                 235                 240
```

```
Thr Glu Trp Gly Ala Asn Gln Ile Gly Arg Ile Thr Asn Asp Lys Thr
            245                 250                 255

Ile Gln Glu Tyr Gln Leu Gln Thr Glu Asn Ala Glu Pro His Gly Ile
        260                 265                 270

Thr Phe Gly Lys Asp Gly Ser Val Trp Phe Ala Leu Lys Cys Lys Ile
    275                 280                 285

Gly Lys Leu Asn Leu Asn Glu
    290                 295

<210> SEQ ID NO 7
<211> LENGTH: 7
<212> TYPE: PRT
<213> ORGANISM: Staphyloccocus

<400> SEQUENCE: 7

Lys Ser Ile Leu Glu Asn Val
1               5

<210> SEQ ID NO 8
<211> LENGTH: 10
<212> TYPE: PRT
<213> ORGANISM: Staphyloccocus
<220> FEATURE:
<223> OTHER INFORMATION: Xaa at position 3 is a Thr/Ser and Xaa at
      position 6 is an Ile/Val

<400> SEQUENCE: 8

Asn Tyr Xaa Asn Tyr Xaa Glu Gln Lys Glu
1               5                   10

<210> SEQ ID NO 9
<211> LENGTH: 9
<212> TYPE: PRT
<213> ORGANISM: Staphyloccocus

<400> SEQUENCE: 9

Ile Met Asn Gly Ala Asn His Arg Met
1               5

<210> SEQ ID NO 10
<211> LENGTH: 7
<212> TYPE: PRT
<213> ORGANISM: Staphyloccocus

<400> SEQUENCE: 10

Gly Asn Asp Val Trp Ile Gly
1               5

<210> SEQ ID NO 11
<211> LENGTH: 21
<212> TYPE: DNA
<213> ORGANISM: Staphyloccocus

<400> SEQUENCE: 11
aarwsyatyt tagaaaatgt t                                         21

<210> SEQ ID NO 12
<211> LENGTH: 30
<212> TYPE: DNA
<213> ORGANISM: Staphyloccocus

<400> SEQUENCE: 12
aattataswa actatrtwga gcaaaaagaa                                30
```

```
<210> SEQ ID NO 13
<211> LENGTH: 27
<212> TYPE: DNA
<213> ORGANISM: Staphyloccocus

<400> SEQUENCE: 13
atwatgaatg gkgcwaayca tmgdatg                                    27

<210> SEQ ID NO 14
<211> LENGTH: 21
<212> TYPE: DNA
<213> ORGANISM: Staphyloccocus

<400> SEQUENCE: 14
ggraaygatg tdtggatwgg w                                          21

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 15
aagtcgactg acaatatgag tggtgg                                     26

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 16
ctgcagatgc ctcaacagca tcgatatcc                                  29

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 17
atgaattcgc aaatcagcaa gg                                         22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 18
tcgtctcgag ctctaggtcc                                            20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 19
cagcagtcta gatcagagtg g                                          21
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 20
catacggatc cacctttcc                                            20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 21
gaaatggttg ggagaagcat acc                                       23

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 22
cagcaatcgc gcccgtttg                                            19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 23
aatcggcaga attacaaacg                                           20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
cgttcccaat ttccgtgtta cc                                        22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 25
gtttctatgc tgatctgaat c                                         21

<210> SEQ ID NO 26
<211> LENGTH: 22
<212> TYPE: DNA
<213> ORGANISM: Artificial Sequence
<220> FEATURE:

<223> OTHER INFORMATION: Description of Artificial Sequence: primer

<400> SEQUENCE: 26
gtcgtttgta attctgccga tt    22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 27
ggtctaaatg gcgatatatg g    21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 28
ttcgaattct tttatcctac c    21

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 29
gcttggcaaa agcaacc    17

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: primer

<400> SEQUENCE: 30
ttggatcagg gcc    13

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 31
caattgttca gctagg    16

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
tacaccattg ttacc    15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 33
gattcagatg ttccc                                              15

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 34
gttgctttcg tagaagc                                            17

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 35
ggttcatcta cgagc                                              15

<210> SEQ ID NO 36
<211> LENGTH: 13
<212> TYPE: DNA
<213> ORGANISM: Artificial Sequence
<220> FEATURE:
<223> OTHER INFORMATION: Description of Artificial Sequence: primer

<400> SEQUENCE: 36
gccaactcca ttc                                                13

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 37
gaaggtgcct gatcc                                              15

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 38
tgaatatagg atag                                               14

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: primer

```
<400> SEQUENCE: 39
caattagaag aaccac                                                      16

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 40
gaattcattc tatgg                                                       15

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 41
caaggaatga ttaagcc                                                     17

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 42
tcatggtcgc aatg                                                        14

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 43
gttatgtcat cctc                                                        14

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 44
ggatatcgat gctg                                                        14

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 45
cctagctgaa caattg                                                      16

<210> SEQ ID NO 46
<211> LENGTH: 13
```

<212> TYPE: DNA
<213> ORGANISM: Artificial Sequence
<220> FEATURE:
<223> OTHER INFORMATION: Description of Artificial Sequence: primer

<400> SEQUENCE: 46
atactagaaa tgc                                                         13

<210> SEQ ID NO 47
<211> LENGTH: 2411
<212> TYPE: DNA
<213> ORGANISM: Staphyloccocus
<220> FEATURE:
<221> NAME/KEY: CDS
<222> LOCATION: (700)..(2355)
<220> FEATURE:
<221> NAME/KEY: CDS
<222> LOCATION: (2388)..(2411)

<400> SEQUENCE: 47
aagctttaat taagttagca gaagattatg gagtaatact aagaacaagt gatagtagta      60
ctaaagaaca agcaaaagaa caagctaaag atgatataat tgacttatta aaagagcaat     120
tagaatatga aaaagatcga aatgaaaaac tatcaaaact taacgataat ttattggaac     180
agttagataa aaatcaaaca ttattagatc agcaacaaag attaagtctt aatgatcaaa     240
atagtatcaa aatgttagaa tcagaattag aagaaaaaaa gaagaaaaag aagaaaaaga     300
aactaagtgg tatcatgtat tccagagaaa aaataatta tatattaaaa tgagatacaa      360
caaatgaatt agtttgtttc aataggaatt tggtaaaacc catgtacata aactttttaa     420
tttagtataa ttaaataaac aaagaaatcg aaagggtgaa atattaataa aatgatcaaa     480
taatccgtca ctaaaaagaa aattaaatat attggaaaga ttttacctaa tatatttatg     540
tctatttatt atgattggat agtttgttta tttgttatat ttcacttata taaactatcc     600 tctatttaa aaaaaggagg attttttat gcttttgttt atttgttata tttcacttat      660
ataaactatc ctctatttta aaaaaggag gatttttt atg ctt aaa atc gac        714
                                          Met Leu Lys Ile Asp
                                           1               5 atg aag aat gta aaa aaa tat tat gca gat aaa tta att tta aat ata      762
Met Lys Asn Val Lys Lys Tyr Tyr Ala Asp Lys Leu Ile Leu Asn Ile
             10                  15                  20 aaa gaa cta aag att tat agt ggg gat aaa ata ggt att gta ggt aag      810
Lys Glu Leu Lys Ile Tyr Ser Gly Asp Lys Ile Gly Ile Val Gly Lys
         25                  30                  35 aat gga gtt ggc aaa aca aca ctt tta aaa ata ata aaa gga cta ata      858
Asn Gly Val Gly Lys Thr Thr Leu Leu Lys Ile Ile Lys Gly Leu Ile
     40                  45                  50 gag att gac gaa gga aat ata att ata agt gaa aaa aca act att aaa      906
Glu Ile Asp Glu Gly Asn Ile Ile Ile Ser Glu Lys Thr Thr Ile Lys
 55                  60                  65 tat atc tct caa tta gaa gaa cca cat agt aag ata att gat gga aaa      954
Tyr Ile Ser Gln Leu Glu Glu Pro His Ser Lys Ile Ile Asp Gly Lys
         70                  75                  80                  85 tat gct tca ata ttt caa gtt gaa aat aag tgg aat gac aat atg agt     1002
Tyr Ala Ser Ile Phe Gln Val Glu Asn Lys Trp Asn Asp Asn Met Ser
             90                  95                 100 ggt ggt gaa aaa act aga ttt aaa cta gca gag gga ttt caa gat caa     1050
Gly Gly Glu Lys Thr Arg Phe Lys Leu Ala Glu Gly Phe Gln Asp Gln
        105                 110                 115 tgt tct tta atg ctc gta gat gaa cct aca agt aat tta gat atc gaa     1098
Cys Ser Leu Met Leu Val Asp Glu Pro Thr Ser Asn Leu Asp Ile Glu

```
                 120                      125                      130
gga  ata  gag  ttg  ata  aca  aat  act  ttt  aaa  gag  tac  cgt  gat  act  ttt           1146
Gly  Ile  Glu  Leu  Ile  Thr  Asn  Thr  Phe  Lys  Glu  Tyr  Arg  Asp  Thr  Phe
135                 140                      145 ttg  gta  gta  tct  cat  gat  aga  att  ttt  tta  gat  caa  gtt  tgt  aca  aaa           1194
Leu  Val  Val  Ser  His  Asp  Arg  Ile  Phe  Leu  Asp  Gln  Val  Cys  Thr  Lys
150                 155                      160                      165 att  ttt  gaa  att  gaa  aat  gga  tat  att  aga  gaa  ttc  atc  ggt  aat  tat           1242
Ile  Phe  Glu  Ile  Glu  Asn  Gly  Tyr  Ile  Arg  Glu  Phe  Ile  Gly  Asn  Tyr
                    170                      175                      180 aca  aac  tat  ata  gag  caa  aaa  gaa  atg  ctt  cta  cga  aag  caa  caa  gaa           1290
Thr  Asn  Tyr  Ile  Glu  Gln  Lys  Glu  Met  Leu  Leu  Arg  Lys  Gln  Gln  Glu
               185                      190                      195 gaa  tac  gaa  aag  tat  aat  tct  aaa  aga  aag  caa  ttg  gag  caa  gct  ata           1338
Glu  Tyr  Glu  Lys  Tyr  Asn  Ser  Lys  Arg  Lys  Gln  Leu  Glu  Gln  Ala  Ile
               200                      205                      210 aag  cta  aaa  gag  aat  aag  gcg  caa  gga  atg  att  aag  ccc  cct  tca  aaa           1386
Lys  Leu  Lys  Glu  Asn  Lys  Ala  Gln  Gly  Met  Ile  Lys  Pro  Pro  Ser  Lys
215                 220                      225 aca  atg  gga  aca  tct  gaa  tct  aga  ata  tgg  aaa  atg  caa  cat  gct  act           1434
Thr  Met  Gly  Thr  Ser  Glu  Ser  Arg  Ile  Trp  Lys  Met  Gln  His  Ala  Thr
230                 235                      240                      245 aaa  caa  aaa  aag  atg  cat  aga  aat  acg  aaa  tcg  ttg  gaa  aca  cga  ata           1482
Lys  Gln  Lys  Lys  Met  His  Arg  Asn  Thr  Lys  Ser  Leu  Glu  Thr  Arg  Ile
                    250                      255                      260 gat  aaa  tta  aat  cat  gta  gaa  aaa  ata  aaa  gag  ctt  cct  tct  att  aaa           1530
Asp  Lys  Leu  Asn  His  Val  Glu  Lys  Ile  Lys  Glu  Leu  Pro  Ser  Ile  Lys
               265                      270                      275 atg  gat  tta  cct  aat  aga  gag  caa  ttt  cat  ggt  cgc  aat  gta  att  agt           1578
Met  Asp  Leu  Pro  Asn  Arg  Glu  Gln  Phe  His  Gly  Arg  Asn  Val  Ile  Ser
               280                      285                      290 tta  aaa  aac  tta  tct  ata  aaa  ttt  aat  aat  caa  ttt  ctt  tgg  aga  gat           1626
Leu  Lys  Asn  Leu  Ser  Ile  Lys  Phe  Asn  Asn  Gln  Phe  Leu  Trp  Arg  Asp
295                 300                      305 gct  tca  ttt  gtc  att  aaa  ggt  gga  gaa  aag  gtt  gct  ata  att  ggt  aac           1674
Ala  Ser  Phe  Val  Ile  Lys  Gly  Gly  Glu  Lys  Val  Ala  Ile  Ile  Gly  Asn
310                 315                      320                      325 aat  ggt  gta  gga  aaa  aca  aca  ttg  ttg  aag  ctg  att  cta  gaa  aaa  gta           1722
Asn  Gly  Val  Gly  Lys  Thr  Thr  Leu  Leu  Lys  Leu  Ile  Leu  Glu  Lys  Val
                    330                      335                      340 gaa  tca  gta  ata  ata  tca  cca  tca  gtt  aaa  att  gga  tac  gtc  agt  caa           1770
Glu  Ser  Val  Ile  Ile  Ser  Pro  Ser  Val  Lys  Ile  Gly  Tyr  Val  Ser  Gln
               345                      350                      355 aac  tta  gat  gtt  cta  caa  tct  cat  aaa  tct  atc  tta  gaa  aat  gtt  atg           1818
Asn  Leu  Asp  Val  Leu  Gln  Ser  His  Lys  Ser  Ile  Leu  Glu  Asn  Val  Met
               360                      365                      370 tct  acc  tcc  att  caa  gat  gaa  aca  ata  gca  aga  att  gtt  cta  gca  aga           1866
Ser  Thr  Ser  Ile  Gln  Asp  Glu  Thr  Ile  Ala  Arg  Ile  Val  Leu  Ala  Arg
               375                      380                      385 tta  cat  ttt  tat  cgc  aat  gat  gtt  cat  aaa  gaa  ata  aat  gtt  ttg  agt           1914
Leu  His  Phe  Tyr  Arg  Asn  Asp  Val  His  Lys  Glu  Ile  Asn  Val  Leu  Ser
390                 395                      400                      405 ggt  gga  gaa  caa  ata  aag  gtt  gct  ttt  gcc  aag  cta  ttt  gtt  agc  gat           1962
Gly  Gly  Glu  Gln  Ile  Lys  Val  Ala  Phe  Ala  Lys  Leu  Phe  Val  Ser  Asp
                    410                      415                      420 tgt  aat  aca  tta  att  ctt  gat  gaa  cca  aca  aac  tat  ttg  gat  atc  gat           2010
Cys  Asn  Thr  Leu  Ile  Leu  Asp  Glu  Pro  Thr  Asn  Tyr  Leu  Asp  Ile  Asp
               425                      430                      435 gct  gtt  gag  gca  tta  gaa  gaa  ttg  tta  att  acc  tat  gaa  ggt  gtt  gtg           2058
```

```
Ala Val Glu Ala Leu Glu Glu Leu Leu Ile Thr Tyr Glu Gly Val Val
        440                 445                 450 tta ttt gct tcc cat gat aaa aaa ttt ata caa aac cta gct gaa caa    2106
Leu Phe Ala Ser His Asp Lys Lys Phe Ile Gln Asn Leu Ala Glu Gln
        455                 460                 465 ttg tta ata ata gaa aat aat aaa gtg aaa aaa ttc gaa gga aca tat    2154
Leu Leu Ile Ile Glu Asn Asn Lys Val Lys Lys Phe Glu Gly Thr Tyr
470                 475                 480                 485 ata gaa tat tta aaa att aaa gat aaa cca aaa tta aat aca aat gaa    2202
Ile Glu Tyr Leu Lys Ile Lys Asp Lys Pro Lys Leu Asn Thr Asn Glu
            490                 495                 500 aaa gaa ctc aaa gaa aaa aag atg ata cta gaa atg caa att tca tca    2250
Lys Glu Leu Lys Glu Lys Lys Met Ile Leu Glu Met Gln Ile Ser Ser
                505                 510                 515 tta tta agt aaa atc tca atg gaa gaa aat gaa gaa aaa aac aaa gaa    2298
Leu Leu Ser Lys Ile Ser Met Glu Glu Asn Glu Glu Lys Asn Lys Glu
            520                 525                 530 tta gat gaa aag tac aaa ttg aaa tta aaa gaa ttg aaa agc cta aat    2346
Leu Asp Glu Lys Tyr Lys Leu Lys Leu Lys Glu Leu Lys Ser Leu Asn
535                 540                 545 aaa aat att taaaataaat tatattaata ggaggtttaa aa atg aaa tat ggc    2399
Lys Asn Ile                                      Met Lys Tyr Gly
550                                                1 cct gat cca aat                                                    2411
Pro Asp Pro Asn
  5

<210> SEQ ID NO 48
<211> LENGTH: 8
<212> TYPE: PRT
<213> ORGANISM: Staphyloccocus

<400> SEQUENCE: 48

Met Lys Tyr Gly Pro Asp Pro Asn
  1               5

<210> SEQ ID NO 49
<211> LENGTH: 522
<212> TYPE: PRT
<213> ORGANISM: Staphyloccocus

<400> SEQUENCE: 49

Met Lys Ile Met Leu Glu Gly Leu Asn Ile Lys His Tyr Val Gln Asp
  1               5                  10                  15

Arg Leu Leu Leu Asn Ile Asn Arg Leu Lys Ile Tyr Gln Asn Asp Arg
                 20                  25                  30

Ile Gly Leu Ile Gly Lys Asn Gly Ser Gly Lys Thr Thr Leu Leu His
             35                  40                  45

Ile Leu Tyr Lys Lys Ile Val Pro Glu Glu Gly Ile Val Lys Gln Phe
         50                  55                  60

Ser His Cys Glu Leu Ile Pro Gln Leu Lys Leu Ile Glu Ser Thr Lys
 65                  70                  75                  80

Ser Gly Gly Glu Val Thr Arg Asn Tyr Ile Arg Gln Ala Leu Asp Lys
                 85                  90                  95

Asn Pro Glu Leu Leu Leu Ala Asp Glu Pro Thr Thr Asn Leu Asp Asn
            100                 105                 110

Asn Tyr Ile Glu Lys Leu Glu Gln Asp Leu Lys Asn Trp His Gly Ala
        115                 120                 125

Phe Ile Ile Val Ser His Asp Arg Ala Phe Leu Asp Asn Leu Cys Thr
```

```
                130                 135                 140
Thr Ile Trp Glu Ile Asp Glu Gly Arg Ile Thr Glu Tyr Lys Gly Asn
145                 150                 155                 160

Tyr Ser Asn Tyr Val Glu Gln Lys Glu Leu Glu Arg His Arg Glu Glu
                165                 170                 175

Leu Glu Tyr Glu Lys Tyr Glu Lys Glu Lys Lys Arg Leu Glu Lys Ala
                180                 185                 190

Ile Asn Ile Lys Glu Gln Lys Ala Gln Arg Ala Thr Lys Lys Pro Lys
                195                 200                 205

Asn Leu Ser Leu Ser Glu Gly Lys Ile Lys Gly Ala Lys Pro Tyr Phe
210                 215                 220

Ala Gly Lys Gln Lys Lys Leu Arg Lys Thr Val Lys Ser Leu Glu Thr
225                 230                 235                 240

Arg Leu Glu Lys Leu Glu Ser Val Glu Lys Arg Asn Glu Leu Pro Pro
                245                 250                 255

Leu Lys Met Asp Leu Val Asn Leu Glu Ser Val Lys Asn Arg Thr Ile
                260                 265                 270

Ile Arg Gly Glu Asp Val Ser Gly Thr Ile Glu Gly Arg Val Leu Trp
                275                 280                 285

Lys Ala Lys Ser Phe Ser Ile Arg Gly Gly Asp Lys Met Ala Ile Ile
                290                 295                 300

Gly Ser Asn Gly Thr Gly Lys Thr Thr Phe Ile Lys Lys Ile Val His
305                 310                 315                 320

Gly Asn Pro Gly Ile Ser Leu Ser Pro Ser Val Lys Ile Gly Tyr Phe
                325                 330                 335

Ser Gln Lys Ile Asp Thr Leu Glu Leu Asp Lys Ser Ile Leu Glu Asn
                340                 345                 350

Val Gln Ser Ser Gln Gln Asn Glu Thr Leu Ile Arg Thr Ile Leu
                355                 360                 365

Ala Arg Met His Phe Phe Arg Asp Asp Val Tyr Lys Pro Ile Ser Val
                370                 375                 380

Leu Ser Gly Gly Glu Arg Val Lys Val Ala Leu Thr Lys Val Phe Leu
385                 390                 395                 400

Ser Glu Val Asn Thr Leu Val Leu Asp Glu Pro Thr Asn Phe Leu Asp
                405                 410                 415

Met Glu Ala Ile Glu Ala Phe Glu Ser Leu Leu Lys Glu Tyr Asn Gly
                420                 425                 430

Ser Ile Ile Phe Val Ser His Asp Arg Lys Phe Ile Glu Lys Val Ala
                435                 440                 445

Thr Arg Ile Met Thr Ile Asp Asn Lys Glu Ile Lys Ile Phe Asp Gly
                450                 455                 460

Thr Tyr Glu Gln Phe Lys Gln Ala Glu Lys Pro Thr Arg Asn Ile Lys
465                 470                 475                 480

Glu Asp Lys Lys Leu Leu Glu Thr Lys Ile Thr Glu Val Leu Ser
                485                 490                 495

Arg Leu Ser Ile Glu Pro Ser Glu Glu Leu Gln Glu Phe Gln Asn
                500                 505                 510

Leu Ile Asn Glu Lys Arg Asn Leu Asp Lys
                515                 520

<210> SEQ ID NO 50
<211> LENGTH: 1607
<212> TYPE: DNA
<213> ORGANISM: Staphyloccocus
```

<220> FEATURE:
<221> NAME/KEY: CDS
<222> LOCATION: (39)..(923)
<220> FEATURE:
<221> NAME/KEY: CDS
<222> LOCATION: (947)..(1582)

<400> SEQUENCE: 50

```
aggagttttt gcgttcaaaa taattgggag gaatgtaa atg aat ttt tat tta gag      56
                                          Met Asn Phe Tyr Leu Glu
                                            1               5 gag ttt aac ttg tct att ccc gat tca ggt cca tac ggt ata act tca       104
Glu Phe Asn Leu Ser Ile Pro Asp Ser Gly Pro Tyr Gly Ile Thr Ser
             10                  15                  20 tca gaa gac gga aag gta tgg ttc aca caa cat aag gca aac aaa atc       152
Ser Glu Asp Gly Lys Val Trp Phe Thr Gln His Lys Ala Asn Lys Ile
         25                  30                  35 agc agt cta gat cag agt ggt agg ata aaa gaa ttc gaa gtt cct acc       200
Ser Ser Leu Asp Gln Ser Gly Arg Ile Lys Glu Phe Glu Val Pro Thr
     40                  45                  50 cct gat gct aaa gtg atg tgt tta att gta tct tca ctt gga gac ata       248
Pro Asp Ala Lys Val Met Cys Leu Ile Val Ser Ser Leu Gly Asp Ile
 55                  60                  65                  70 tgg ttt aca gag aat ggt gca aat aaa atc gga aag ctc tca aaa aaa       296
Trp Phe Thr Glu Asn Gly Ala Asn Lys Ile Gly Lys Leu Ser Lys Lys
                 75                  80                  85 ggt ggc ttt aca gaa tat cca ttg cca cag ccg gat tct ggt cct tac       344
Gly Gly Phe Thr Glu Tyr Pro Leu Pro Gln Pro Asp Ser Gly Pro Tyr
             90                  95                 100 gga ata acg gaa ggt cta aat ggc gat ata tgg ttt acc caa ttg aat       392
Gly Ile Thr Glu Gly Leu Asn Gly Asp Ile Trp Phe Thr Gln Leu Asn
         105                 110                 115 gga gat cgt ata gga aag ttg aca gct gat ggg act att tat gaa tat       440
Gly Asp Arg Ile Gly Lys Leu Thr Ala Asp Gly Thr Ile Tyr Glu Tyr
    120                 125                 130 gat ttg cca aat aag gga tct tat cct gct ttt att act tta ggt tcg       488
Asp Leu Pro Asn Lys Gly Ser Tyr Pro Ala Phe Ile Thr Leu Gly Ser
135                 140                 145                 150 gat aac gca ctt tgg ttc acg gag aac caa aat aat tct att gga agg       536
Asp Asn Ala Leu Trp Phe Thr Glu Asn Gln Asn Asn Ser Ile Gly Arg
                155                 160                 165 att aca aat aca ggg aaa tta gaa gaa tat cct cta cca aca aat gca       584
Ile Thr Asn Thr Gly Lys Leu Glu Glu Tyr Pro Leu Pro Thr Asn Ala
            170                 175                 180 gcg gct cca gtg ggt atc act agt ggt aac gat ggt gca ctc tgg ttt       632
Ala Ala Pro Val Gly Ile Thr Ser Gly Asn Asp Gly Ala Leu Trp Phe
        185                 190                 195 gtc gaa att atg ggc aac aaa ata ggt cga atc act aca act ggt gag       680
Val Glu Ile Met Gly Asn Lys Ile Gly Arg Ile Thr Thr Thr Gly Glu
    200                 205                 210 att agc gaa tat gat att cca act cca aac gca cgt cca cac gct ata       728
Ile Ser Glu Tyr Asp Ile Pro Thr Pro Asn Ala Arg Pro His Ala Ile
215                 220                 225                 230 acc gcg ggg aaa aat agc gaa ata tgg ttt act gaa tgg ggg gca aat       776
Thr Ala Gly Lys Asn Ser Glu Ile Trp Phe Thr Glu Trp Gly Ala Asn
                235                 240                 245 caa atc ggc aga att aca aac gac aaa aca att caa gaa tat caa ctt       824
Gln Ile Gly Arg Ile Thr Asn Asp Lys Thr Ile Gln Glu Tyr Gln Leu
            250                 255                 260 caa aca gaa aat gcg gaa cct cat ggt att acc ttt gga aaa gat gga       872
Gln Thr Glu Asn Ala Glu Pro His Gly Ile Thr Phe Gly Lys Asp Gly
```

-continued

```
              265                 270                 275
tcc gta tgg ttt gca tta aaa tgt aaa att ggg aag ctg aat ttg aac      920
Ser Val Trp Phe Ala Leu Lys Cys Lys Ile Gly Lys Leu Asn Leu Asn
    280                 285                 290 gaa tgagatggga gtgagcaata ttt atg aaa tgg caa aat cag caa ggc ccc    973
Glu                         Met Lys Trp Gln Asn Gln Gln Gly Pro
295                           1                   5 aat cca gaa gaa ata tac cct ata gaa ggt aat aaa cat gtt caa ttt     1021
Asn Pro Glu Glu Ile Tyr Pro Ile Glu Gly Asn Lys His Val Gln Phe
 10                  15                  20                  25 att aaa cca tct ata aca aag ccc aat att tta gtt ggg gaa tat tca     1069
Ile Lys Pro Ser Ile Thr Lys Pro Asn Ile Leu Val Gly Glu Tyr Ser
                 30                  35                  40 tat tac gat agt aaa gat ggt gaa tct ttt gaa agc caa gtt ctt tat     1117
Tyr Tyr Asp Ser Lys Asp Gly Glu Ser Phe Glu Ser Gln Val Leu Tyr
             45                  50                  55 cac tat gaa ttg att ggg gat aaa cta ata tta ggg aag ttt tgt tct     1165
His Tyr Glu Leu Ile Gly Asp Lys Leu Ile Leu Gly Lys Phe Cys Ser
         60                  65                  70 att gga ccc gga acg aca ttt ata atg aat ggg gct aat cat cgt atg     1213
Ile Gly Pro Gly Thr Thr Phe Ile Met Asn Gly Ala Asn His Arg Met
 75                  80                  85 gat ggt tca aca ttt cca ttc aat ctt ttc gga aat ggt tgg gag aag     1261
Asp Gly Ser Thr Phe Pro Phe Asn Leu Phe Gly Asn Gly Trp Glu Lys
 90                  95                 100                 105 cat acc cct aca ttg gaa gac ctt cct tat aag ggt aac acg gaa att     1309
His Thr Pro Thr Leu Glu Asp Leu Pro Tyr Lys Gly Asn Thr Glu Ile
                110                 115                 120 ggg aac gat gtt tgg att gga cga gat gtg aca att atg ccc ggt gta    1357
Gly Asn Asp Val Trp Ile Gly Arg Asp Val Thr Ile Met Pro Gly Val
            125                 130                 135 aaa ata gga aac ggg gct att att gca gca aaa tcg gtt gtg aca aag    1405
Lys Ile Gly Asn Gly Ala Ile Ile Ala Ala Lys Ser Val Val Thr Lys
        140                 145                 150 aac gtt gat cct tat tca gtt gtt ggc ggt aat cct tca cga tta att    1453
Asn Val Asp Pro Tyr Ser Val Val Gly Gly Asn Pro Ser Arg Leu Ile
    155                 160                 165 aag ata agg ttt tcc aag gaa aaa atc gca gca tta cta aaa gta agg    1501
Lys Ile Arg Phe Ser Lys Glu Lys Ile Ala Ala Leu Leu Lys Val Arg
170                 175                 180                 185 tgg tgg gac cta gag ata gag acg ata aat gaa aat att gat tgc atc    1549
Trp Trp Asp Leu Glu Ile Glu Thr Ile Asn Glu Asn Ile Asp Cys Ile
                190                 195                 200 ctg aat ggt gat ata aaa aag gtt aaa aga agt tagaaaacga attttgttta  1602
Leu Asn Gly Asp Ile Lys Lys Val Lys Arg Ser
            205                 210 ggtta                                                              1607
```